US012569235B2

(12) United States Patent
Sauer

(10) Patent No.: US 12,569,235 B2
(45) Date of Patent: Mar. 10, 2026

(54) SURGICAL RETRACTOR ASSEMBLY

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 0 days.

(21) Appl. No.: 18/612,626

(22) Filed: Mar. 21, 2024

(65) Prior Publication Data

US 2024/0315686 A1 Sep. 26, 2024

Related U.S. Application Data

(60) Provisional application No. 63/527,166, filed on Jul. 17, 2023, provisional application No. 63/453,735, filed on Mar. 21, 2023.

(51) Int. Cl.
*A61B 17/02* (2006.01)

(52) U.S. Cl.
CPC ...... *A61B 17/02* (2013.01); *A61B 2017/0287* (2013.01)

(58) Field of Classification Search
CPC .... A61B 2017/0225; A61B 2017/0287; A61B 17/0218; A61B 17/3423; A61B 17/3431; A61B 17/0293; A61B 17/02
See application file for complete search history.

(56) References Cited

U.S. PATENT DOCUMENTS

| | | | |
|---|---|---|---|
| 3,729,006 A | 4/1973 | Wilder et al. | |
| 5,514,076 A | 5/1996 | Ley | |
| 5,795,291 A | 8/1998 | Koros et al. | |
| 5,810,721 A * | 9/1998 | Mueller | A61B 17/0293 600/206 |
| 5,947,896 A | 9/1999 | Sherts et al. | |
| 6,048,309 A * | 4/2000 | Flom | A61B 17/0293 600/206 |
| 6,354,994 B1 | 3/2002 | Rullo et al. | |
| 6,814,700 B1 * | 11/2004 | Mueller | A61B 17/0293 600/206 |
| 7,435,219 B2 * | 10/2008 | Kim | A61B 17/0293 600/233 |
| 7,537,564 B2 * | 5/2009 | Bonadio | A61B 17/0293 600/208 |
| 7,909,761 B2 | 3/2011 | Banchieri et al. | |
| 8,162,827 B2 | 4/2012 | Abdelgany et al. | |
| 8,192,463 B2 | 6/2012 | McLoughlin | |

(Continued)

FOREIGN PATENT DOCUMENTS

| | | |
|---|---|---|
| CN | 201551349 | 8/2010 |
| CN | 202982093 | 6/2013 |

(Continued)

*Primary Examiner* — Jacqueline T Johanas

(74) *Attorney, Agent, or Firm* — Michael E. Coyne

(57) ABSTRACT

A retractor assembly includes a retractor body assembly includes first and second primary retractor blade assemblies and first and second secondary blade assemblies that each have a base portion and a blade portion. The base portions of the blade assemblies may be connected to form a ring, and the ring may be inserted into an incision formed in a patient. The blade portions of the blade assemblies may then be folded towards and secured to a ring assembly, with the blade portions retracting tissue around the incision.

11 Claims, 25 Drawing Sheets

(56)                References Cited

U.S. PATENT DOCUMENTS

| | | | | |
|---|---|---|---|---|
| 8,231,570 B2* | 7/2012 | Ortiz | ................. | A61B 17/3462 |
| | | | | 604/364 |
| 8,246,539 B2 | 8/2012 | Hjelle et al. | | |
| 8,523,769 B2 | 9/2013 | Fehling et al. | | |
| 8,734,336 B2* | 5/2014 | Bonadio | ........... | A61B 17/0293 |
| | | | | 600/203 |
| 8,758,235 B2 | 6/2014 | Jaworek | | |
| 8,911,364 B2 | 12/2014 | Feigenwinter | | |
| 8,961,409 B2 | 2/2015 | O'Prey et al. | | |
| 9,986,988 B2 | 6/2018 | Ferro et al. | | |
| 10,016,189 B2 | 7/2018 | Sauer | | |
| 10,172,603 B2 | 1/2019 | Blain | | |
| 10,307,151 B2* | 6/2019 | Chung | ................. | A61B 90/50 |
| 10,485,677 B2 | 11/2019 | Massengale | | |
| 10,631,841 B2* | 4/2020 | Beger | ............... | A61B 17/0218 |
| 10,751,037 B2 | 8/2020 | Ferro | | |
| 11,147,545 B1* | 10/2021 | Thomas | ............ | A61B 17/3423 |
| 11,259,791 B2 | 3/2022 | Maher et al. | | |
| 11,291,436 B2 | 4/2022 | Tsubouchi | | |
| 11,596,439 B2* | 3/2023 | Coe | ................... | A61B 17/3423 |
| 2005/0197537 A1 | 9/2005 | Bonadio et al. | | |
| 2006/0229636 A1* | 10/2006 | Woodburn, Sr. ... | | A61B 17/3439 |
| | | | | 606/108 |
| 2007/0060939 A1* | 3/2007 | Lancial | ............. | A61B 1/00154 |
| | | | | 606/191 |
| 2007/0156023 A1* | 7/2007 | Frasier | .............. | A61B 17/0293 |
| | | | | 600/233 |
| 2008/0103366 A1* | 5/2008 | Banchieri | ......... | A61B 17/3439 |
| | | | | 600/208 |
| 2009/0024158 A1* | 1/2009 | Viker | ................ | A61B 17/0218 |
| | | | | 600/208 |
| 2010/0191253 A1* | 7/2010 | Oostman, Jr. ...... | | A61B 17/0206 |
| | | | | 606/1 |
| 2010/0211093 A1* | 8/2010 | Abbate | ............. | A61B 17/0206 |
| | | | | 606/196 |
| 2010/0305407 A1 | 12/2010 | Farley | | |
| 2011/0021879 A1* | 1/2011 | Hart | ................... | A61B 17/0293 |
| | | | | 600/207 |
| 2011/0054260 A1* | 3/2011 | Albrecht | ........... | A61B 17/0218 |
| | | | | 600/208 |
| 2011/0144443 A1* | 6/2011 | Shelton, IV | ............ | A61B 1/32 |
| | | | | 600/206 |
| 2012/0143008 A1* | 6/2012 | Wilkins | ............. | A61B 17/0218 |
| | | | | 600/206 |
| 2012/0245424 A1 | 9/2012 | O'Prey et al. | | |
| 2012/0289785 A1* | 11/2012 | Albrecht | ........... | A61B 17/0293 |
| | | | | 600/225 |
| 2013/0066158 A1* | 3/2013 | Rodriguez | ......... | A61B 17/0218 |
| | | | | 600/208 |
| 2014/0275797 A1* | 9/2014 | Ibrahim | ............. | A61B 17/3439 |
| | | | | 600/208 |
| 2014/0316209 A1* | 10/2014 | Overes | .............. | A61B 17/3439 |
| | | | | 600/206 |
| 2015/0359528 A1* | 12/2015 | Strauss | ............. | A61B 17/0218 |
| | | | | 600/201 |
| 2016/0007981 A1 | 1/2016 | Govindarajan et al. | | |
| 2016/0008027 A1* | 1/2016 | Ibrahim | ................ | A61M 25/09 |
| | | | | 600/204 |
| 2016/0015425 A1 | 1/2016 | Bolanos et al. | | |
| 2016/0030239 A1* | 2/2016 | Akura | ................ | A61B 17/0231 |
| | | | | 606/107 |
| 2016/0051244 A1* | 2/2016 | Akura | ................ | A61B 17/0206 |
| | | | | 600/236 |
| 2017/0100118 A1* | 4/2017 | Albrecht | ........... | A61B 17/0293 |
| 2017/0258463 A1* | 9/2017 | Strauss | ............. | A61B 17/0293 |
| 2017/0360424 A1* | 12/2017 | Craft | ................... | A61B 17/122 |
| 2019/0175218 A1* | 6/2019 | Suzuki | .................. | A61B 17/02 |
| 2020/0054315 A1 | 2/2020 | Pell et al. | | |
| 2020/0060671 A1* | 2/2020 | Strauss | ................. | A61B 17/02 |
| 2020/0245856 A1 | 8/2020 | Berry | | |
| 2021/0077088 A1* | 3/2021 | Berry | ....................... | A61B 1/32 |
| 2021/0322000 A1 | 10/2021 | Glambruno et al. | | |
| 2021/0361276 A1* | 11/2021 | Sauer | ................ | A61B 17/0218 |
| 2022/0015519 A1 | 1/2022 | Tsai | | |

FOREIGN PATENT DOCUMENTS

| | | | | | |
|---|---|---|---|---|---|
| CN | 104127211 | A | * | 11/2014 | ........ A61B 17/0206 |
| CN | 211460321 | | | 9/2020 | |
| CN | 111839623 | A | * | 10/2020 | ............ A61B 17/02 |
| CN | 215018129 | | | 12/2021 | |
| CN | 114711849 | A | * | 7/2022 | |
| DE | 000019506266 | | | 9/1996 | |
| GB | 2467960 | A | * | 8/2010 | ........ A61B 17/0218 |
| KR | 20110083836 | | | 7/2011 | |
| KR | 20140114886 | A | * | 1/2012 | |
| KR | 20220090699 | A | * | 12/2020 | |
| KR | 20220006677 | A | * | 3/2022 | |
| RU | 0000178611 | | | 4/2018 | |
| RU | 2674233 | | | 12/2018 | |
| WO | WO-2015164923 | A1 | * | 11/2015 | ............ A61B 17/02 |
| WO | WO-2017083694 | A1 | * | 5/2017 | ....... A61B 17/00234 |
| WO | 2018039326 | | | 3/2018 | |
| WO | WO-2019213582 | A1 | * | 11/2019 | ........ A61B 17/0218 |
| WO | 2022087537 | | | 4/2022 | |

* cited by examiner

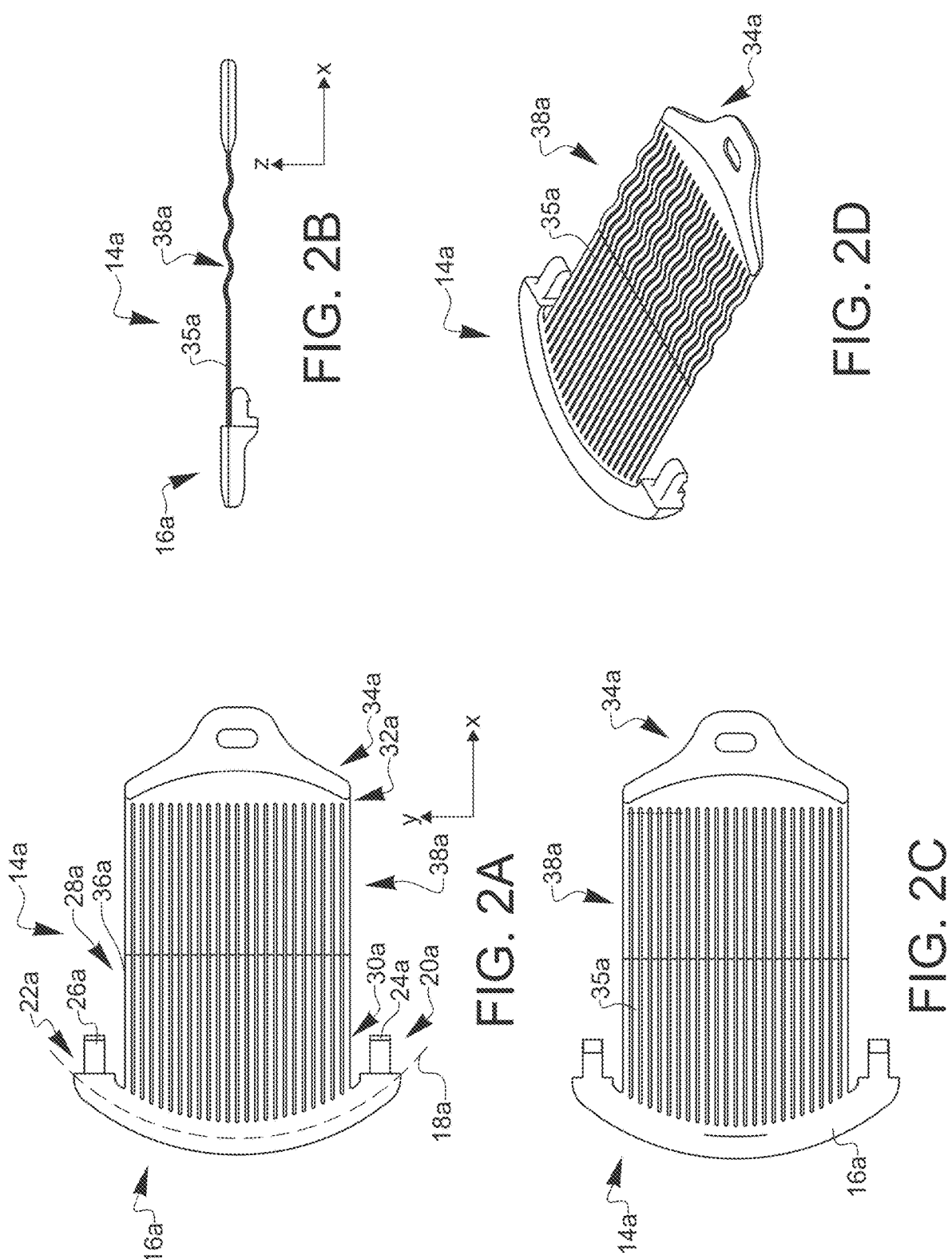

SURGICAL RETRACTOR ASSEMBLY

CROSS-REFERENCE TO RELATED APPLICATIONS

This application claims the benefit of each of U.S. Provisional Patent Application No. 63/453,735, filed Mar. 21, 2023, and U.S. Provisional Patent Application No. 63/527, 166, filed Jul. 17, 2023, the contents of each which is hereby incorporated by reference in its entirety.

FIELD OF THE INVENTION

The claimed invention relates to surgical devices, and more specifically to a surgical retractor assembly and a delivery device for the surgical retractor assembly.

BACKGROUND

A retractor or spreader is a surgical instrument used to separate the edges of a surgical incision/wound or to hold away certain organs and tissues so that body parts underneath may be accessed during surgical operations. A retractor is typically a simple steel tool possessing a curved, hooked, or angled blade, which is manually manipulated to help maintain a desired position of tissue during surgery. More sophisticated retractors may be clamped in place (usually to a tableside frame) or suspended at the end of a robotic arm. Retractors can also be "self-retaining" and no longer need to be held once inserted, having two or more opposing blades or hooks which are separated via spring, ratchet, worm gear or other method. However, conventional retractor assemblies, sue to the stiff nature of the blades, may damage the tissue contacted by the blade. Further, such assemblies are typically large and therefore difficult to position in minimally-invasive procedures.

BRIEF DESCRIPTION OF THE DRAWINGS

FIGS. 2A to 2D are various view of an embodiment of a first primary retractor blade assembly of a retractor body assembly;

DETAILED DESCRIPTION OF THE INVENTION

Figures 1A, 1B:
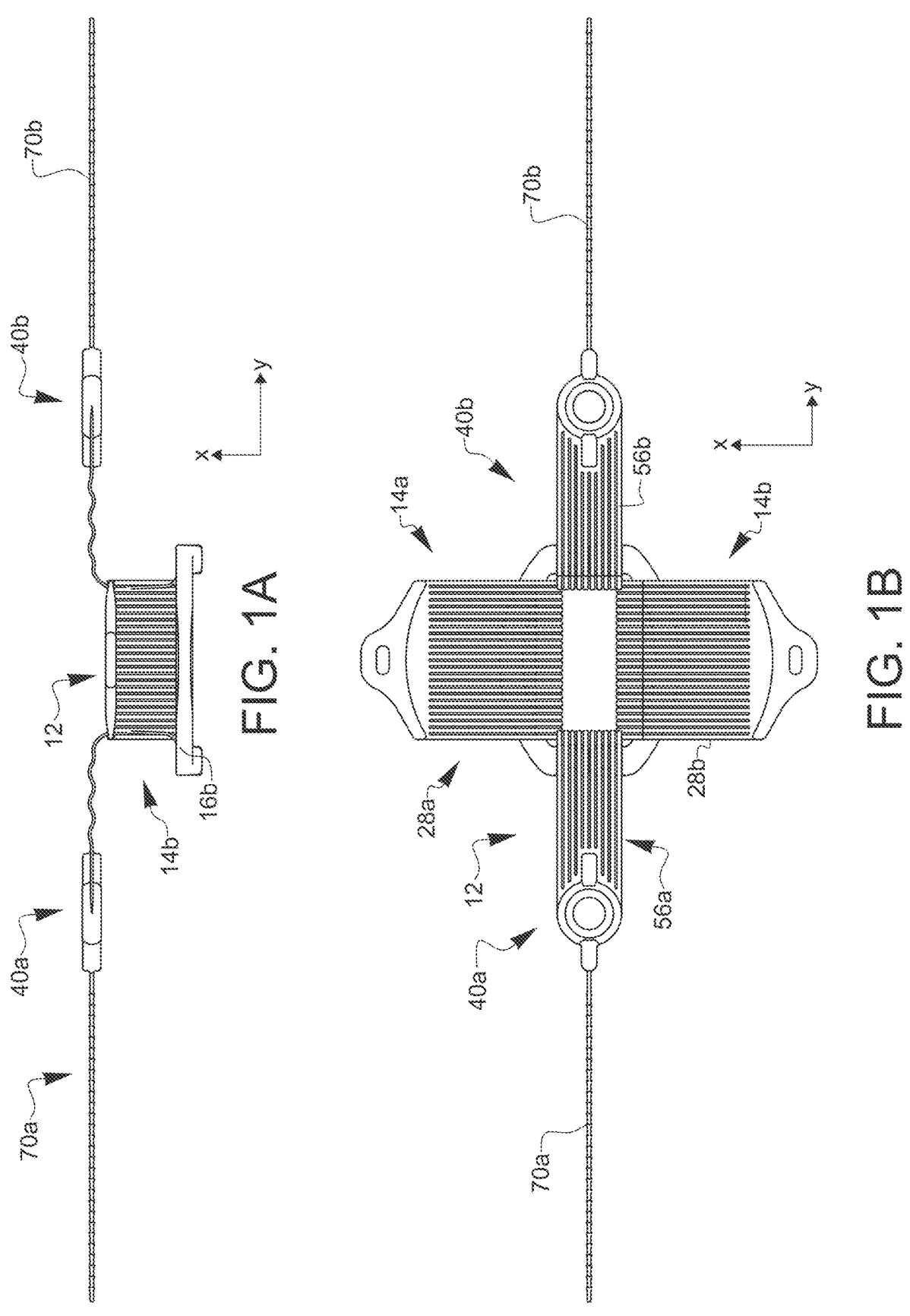
FIGS. 1A to 1E are various view of an embodiment of a retractor body assembly of a retractor assembly.

As illustrated in FIGS. 1A to 1E, an embodiment of a retractor assembly 10 includes a retractor body assembly 12 that includes a first primary retractor blade assembly 14a having a base portion 16a extending along a base axis 18a from a first end 20a to a second end 22a, the base portion including a first engagement feature 24a disposed at a first portion of the base portion 16a and a second engagement feature 26a disposed at a second portion of the base portion 16a. The base axis 18a may be non-linear and may have an arcuate shape or the shape of a segment of a circle. The first engagement feature 24a may be disposed at or adjacent to the first end 20a of the base portion 16a and the second engagement feature 26a may be disposed at or adjacent to the second end 22a of the base portion 16a. Each of the first engagement feature 24a and the second engagement feature 26a may be configured to be coupled to corresponding engagement features of the secondary retractor blade assembly 40a, 40b, as will be described in more detail below. For example, each of the first engagement feature 24a and the second engagement feature 26a may be a protrusion having an undercut portion.

Figures 5, 6:
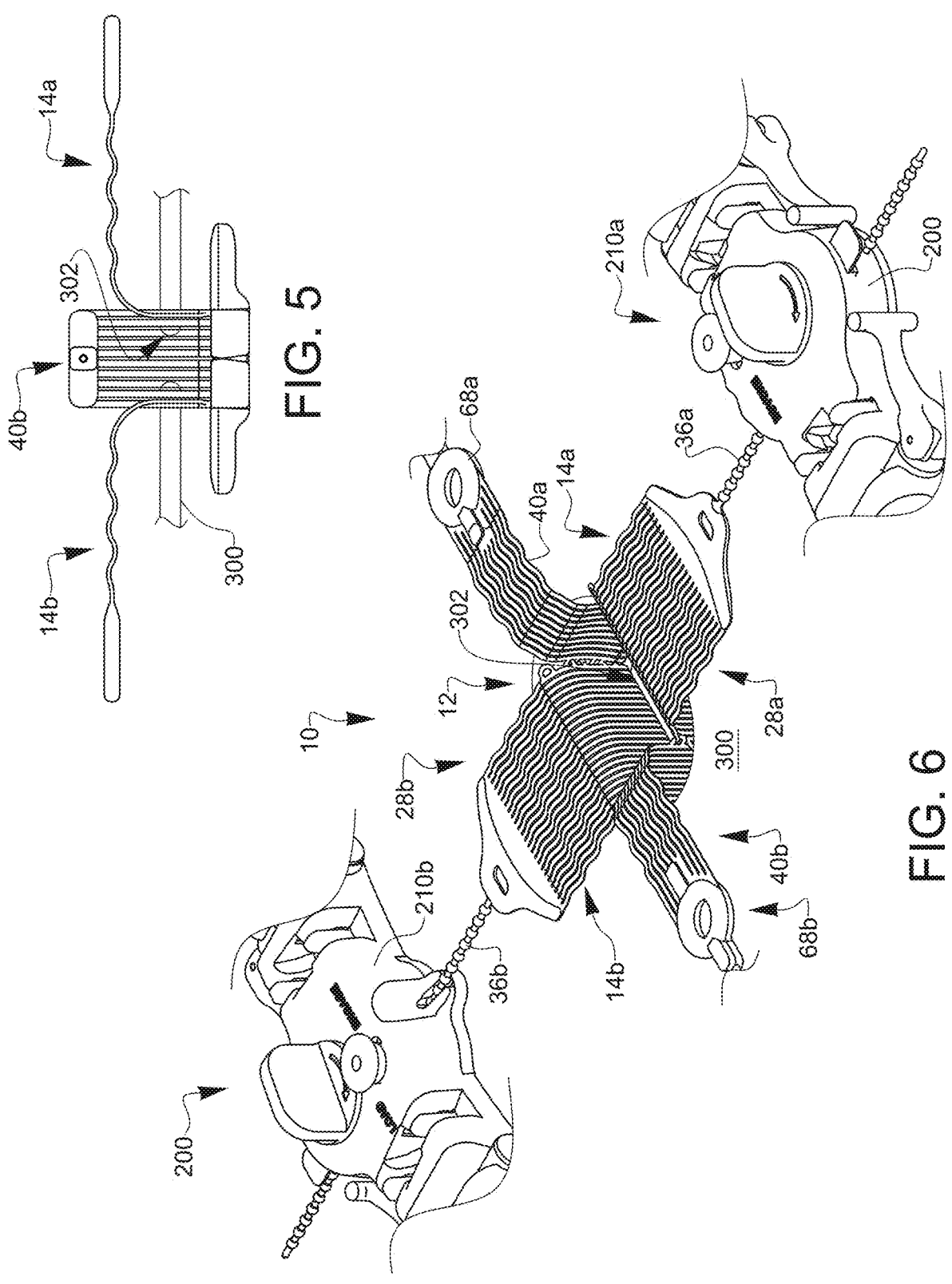
FIG. 5 is a side view of the embodiment of the retractor body assembly of FIG. 1A inserted into an incision of a patient (with the ring assembly omitted for clarity)
FIG. 6 is a perspective view of the embodiment of the retractor body assembly of FIG. 1A inserted into the incision of a patient (with portions of the ring assembly omitted for clarity)

The first primary retractor blade assembly 14a also includes a blade portion 28a extending from a first end 30a to a second end 32a, the first end 30a of the blade portion 28a coupled to a portion of the base portion 16a. The blade portion 28a is configured to be flexible such that the second end 32a of the blade portion 28a is configured to be displaceable relative to the first end 30a such that the second end 32a is capable of being folded away from the first end 30a and anchored to a surgical instrument (such as to a portion 202a of the ring assembly 200 illustrated in FIGS. 4A to 4E), thereby creating a "sling" or pocket that is configured to receive and retract a corresponding portion of a patient's tissue 300, as illustrated in FIG. 5. A coupling portion 34a may be disposed at the second end 32a of the blade portion 28a, and the coupling portion 34a may include an aperture that is configured to be coupled to a portion of a surgical instrument to provide external support for the blade portion 28a, such as a hook portion (not shown) that may be adjustably coupled to the ring assembly 200 illustrated in FIGS. 4A to 4E. The coupling portion 34a may alternatively include an elongated coupling strip 36a that extends from the second end 32a of the blade portion 28a, as illustrated in FIG. 6. The coupling strip 36a may be engaged by an adjustment gear 208a disposed at a portion of the ring assembly 200 such that when the adjustment gear 208a is rotated by a user, a force is provided that incrementally folds the second end 32a away from the first end 30a of the blade portion 28a.

Figures 1C, 1D:
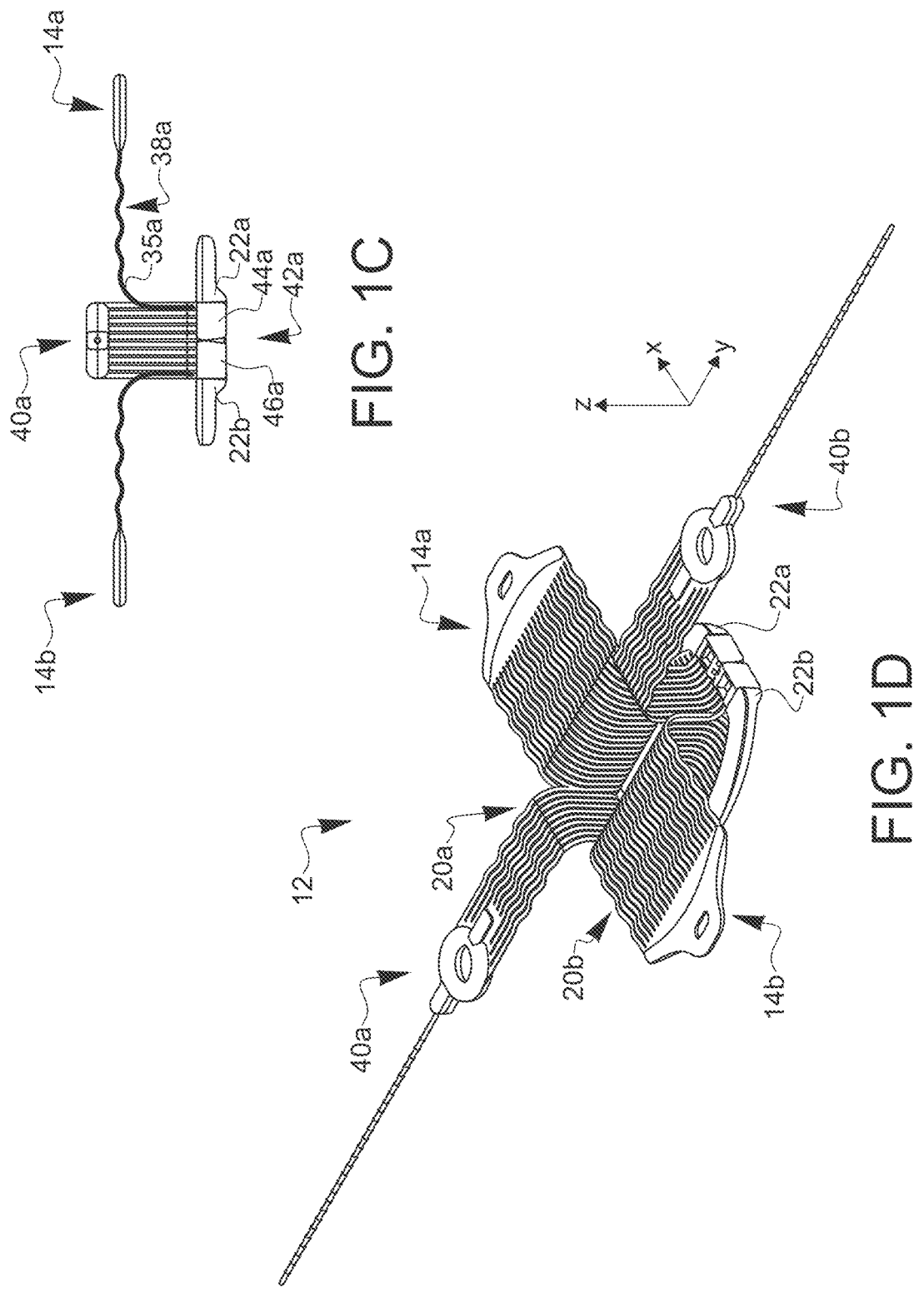

As illustrated in FIG. 2B, at least a first portion 35a of the blade portion 28a may be planar (and may be manufactured in a planar orientation), and the plane may be folded or curved about a single axis when assembled as described and as illustrated in FIG. 1C. A second portion 38a of the blade portion 28a may be non-planar, and the second portion 38a may have a sinusoidal shape (or an undulating or zig-zag) that is configured to expand in a direction along a longitudinal axis (i.e., along or parallel to the X-axis of the reference coordinate system of FIGS. 1A, 1B, 1D, and 2A) of the blade portion 28a. The second portion 38a may act like a spring to allow the blade portion 28a to increase in length when necessary when secured to the ring assembly 200, thereby providing extra flexibility of the blade portion 28a when the blade portion 28a contacts tissue. In some embodiments, the blade portion 28a may include a plurality of elongated tines 36a that each extend from the first end 30a to the second end 32a of the blade portion 28a. However, in some embodiments, the blade portion 28a may not be composed of tines, but may have the shape of an elongated plate. The base portion 16a, blade portion 28a, and coupling portion 34a may be a is a single, unitary part made form a single piece of material, such as a plastic material that may be injection molded as a single part.

The retractor body assembly 12 may also include a second primary retractor blade assembly 14b that may be identical or substantially identical to, and/or a mirror-image of, the first primary retractor blade assembly 14a. Accordingly, all reference numbers corresponding to the first primary retractor blade assembly 14a will be identical for the second primary retractor blade assembly 14b, with the exception that the "a" associated the first primary retractor blade assembly 14a is replaced by a "b" for the second primary retractor blade assembly 14b.

Figure 1E:
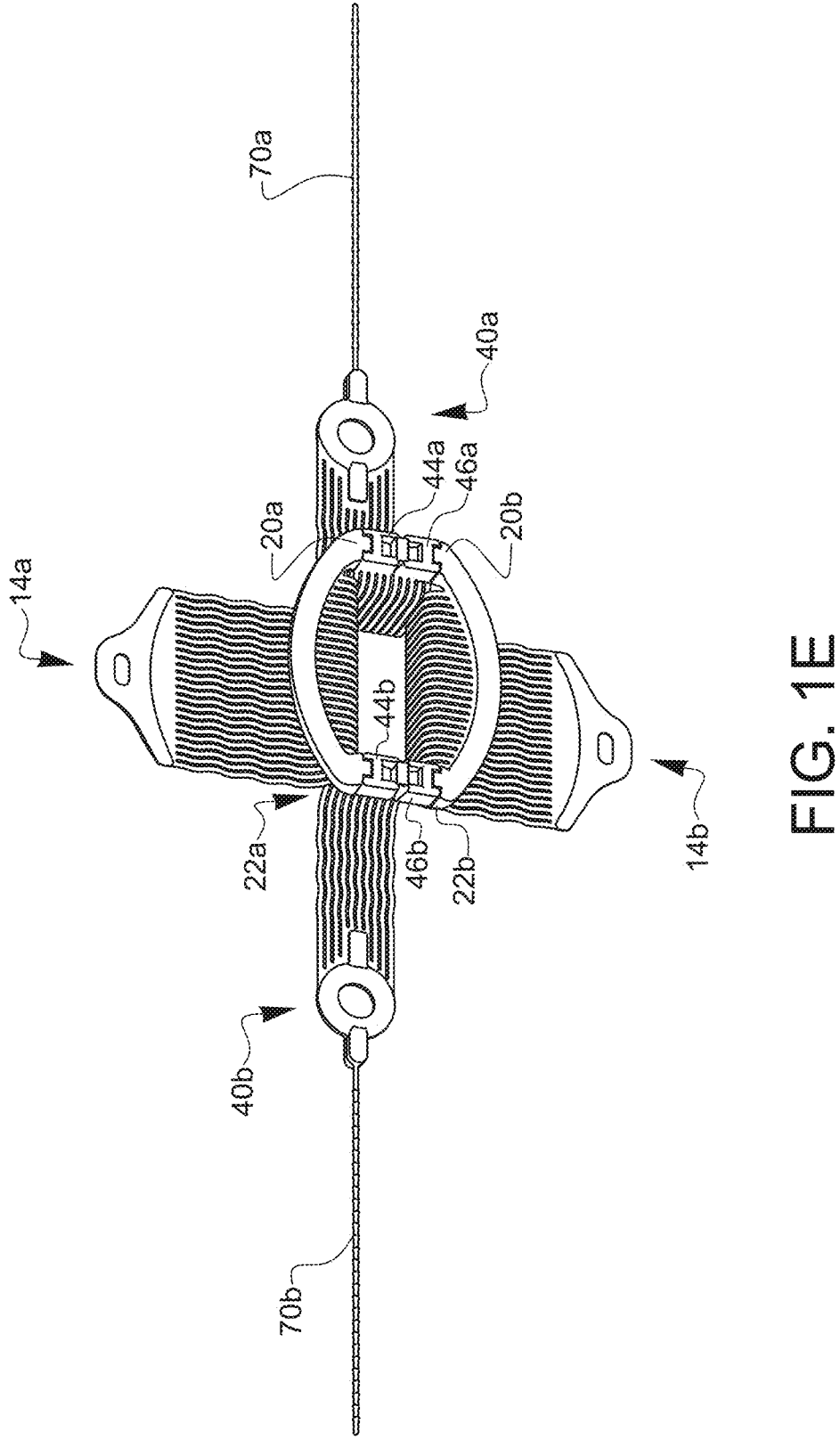
Figures 3A, 3B:
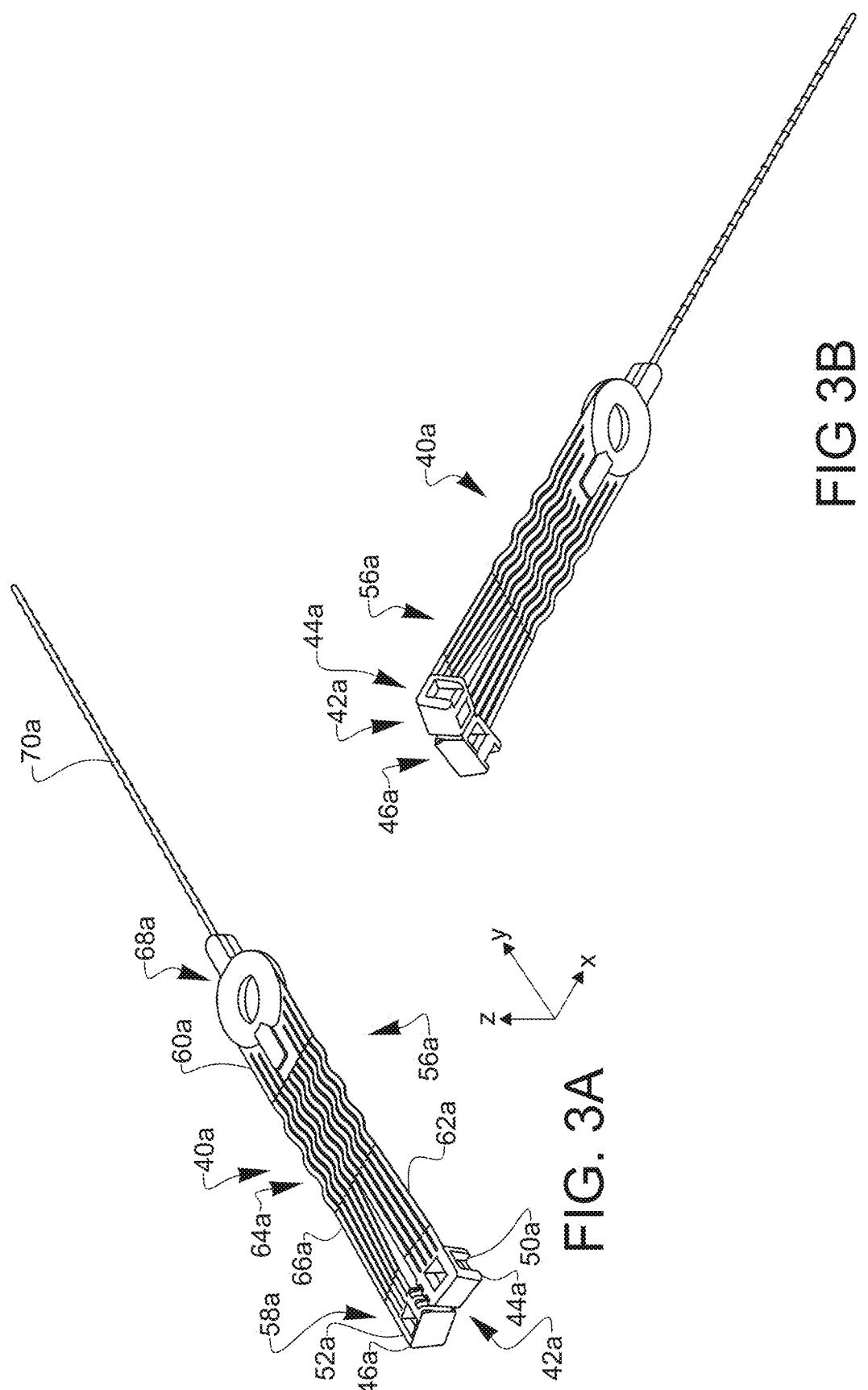
FIGS. 3A to 3E are various view of an embodiment of a first secondary retractor blade assembly of a retractor body assembly.
Figures 3C, 3D, 3E:
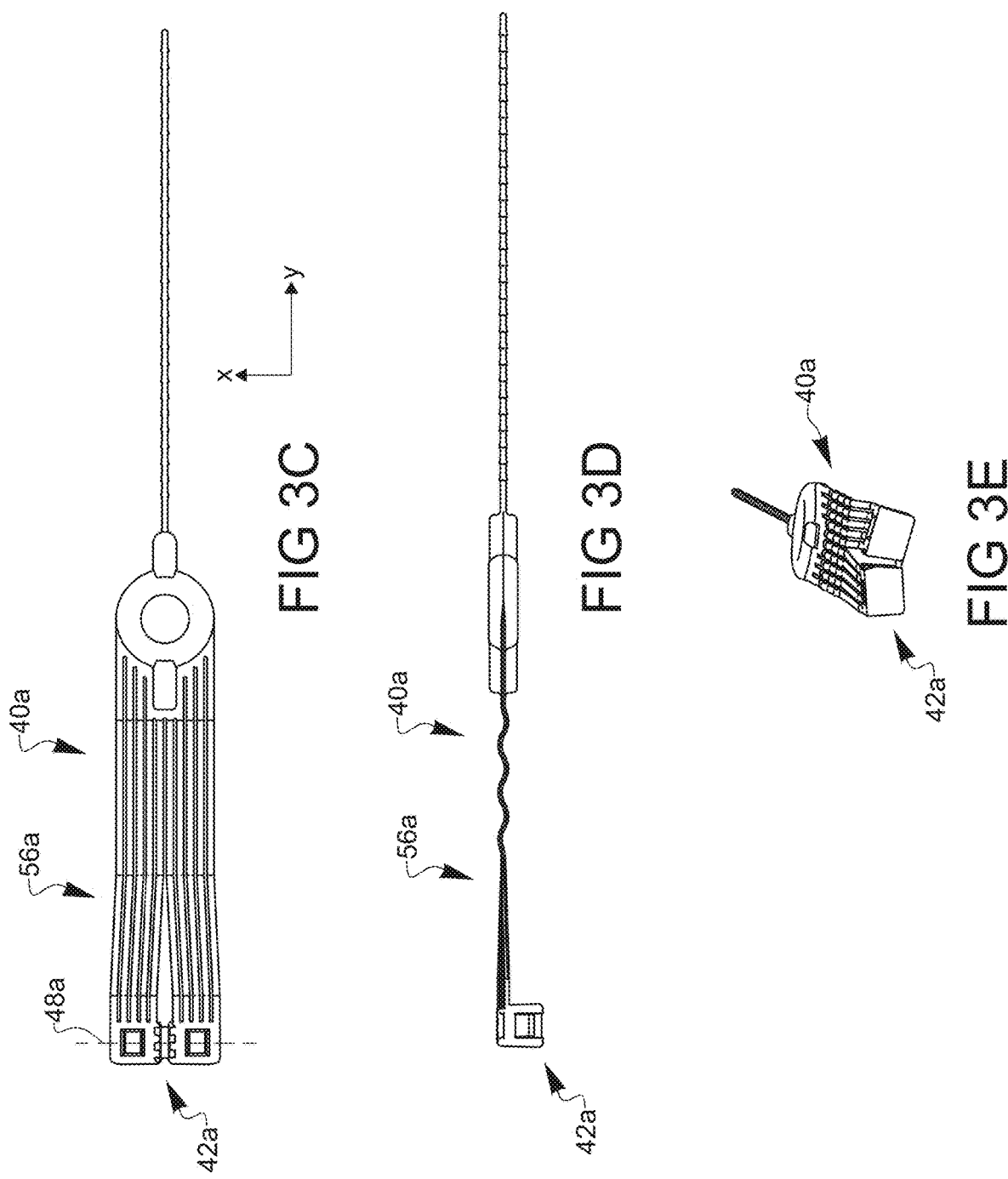
Figure 4A:
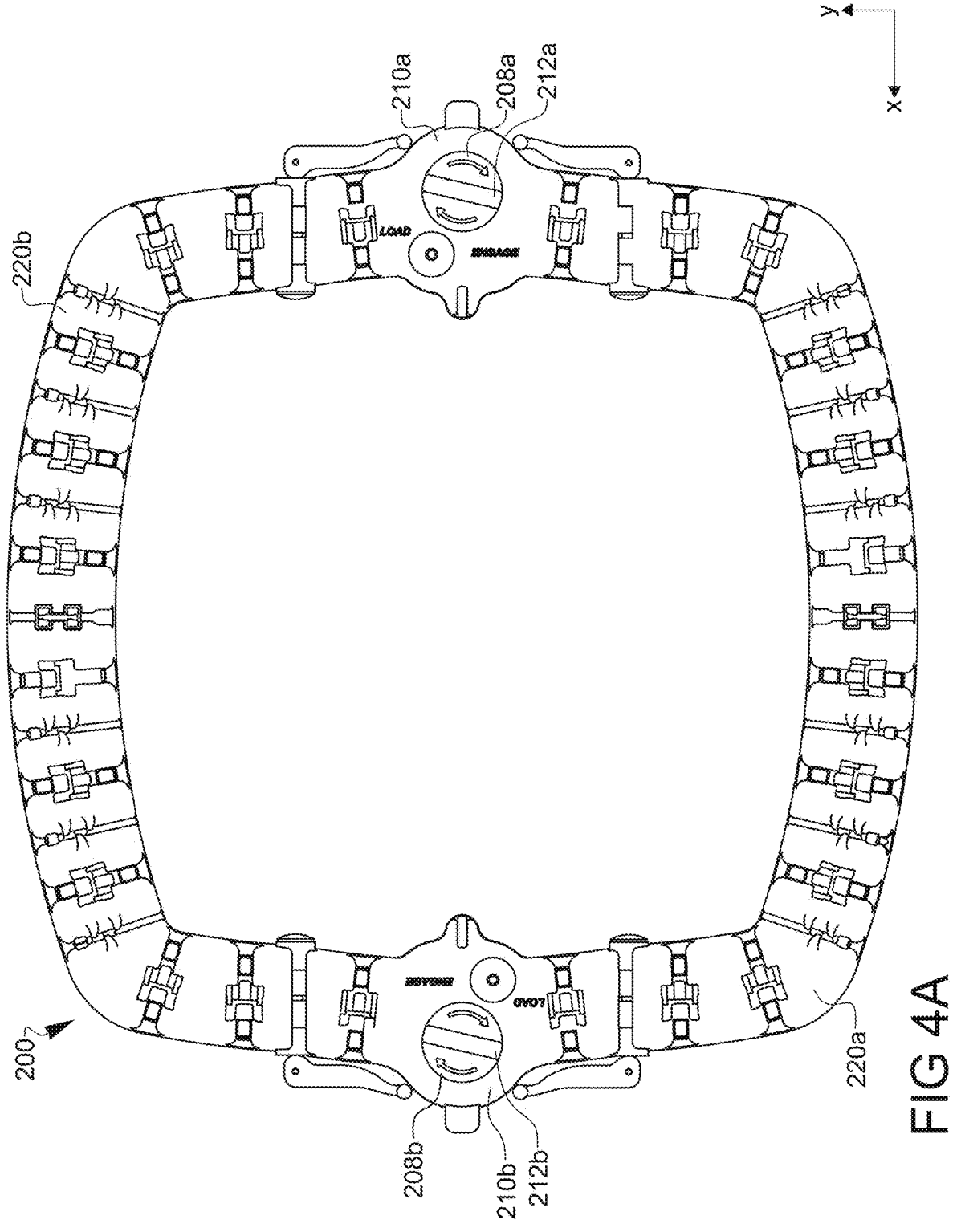
FIGS. 4A to 4E are various view of an embodiment of a ring assembly of a retractor assembly.
Figures 4B, 4C:
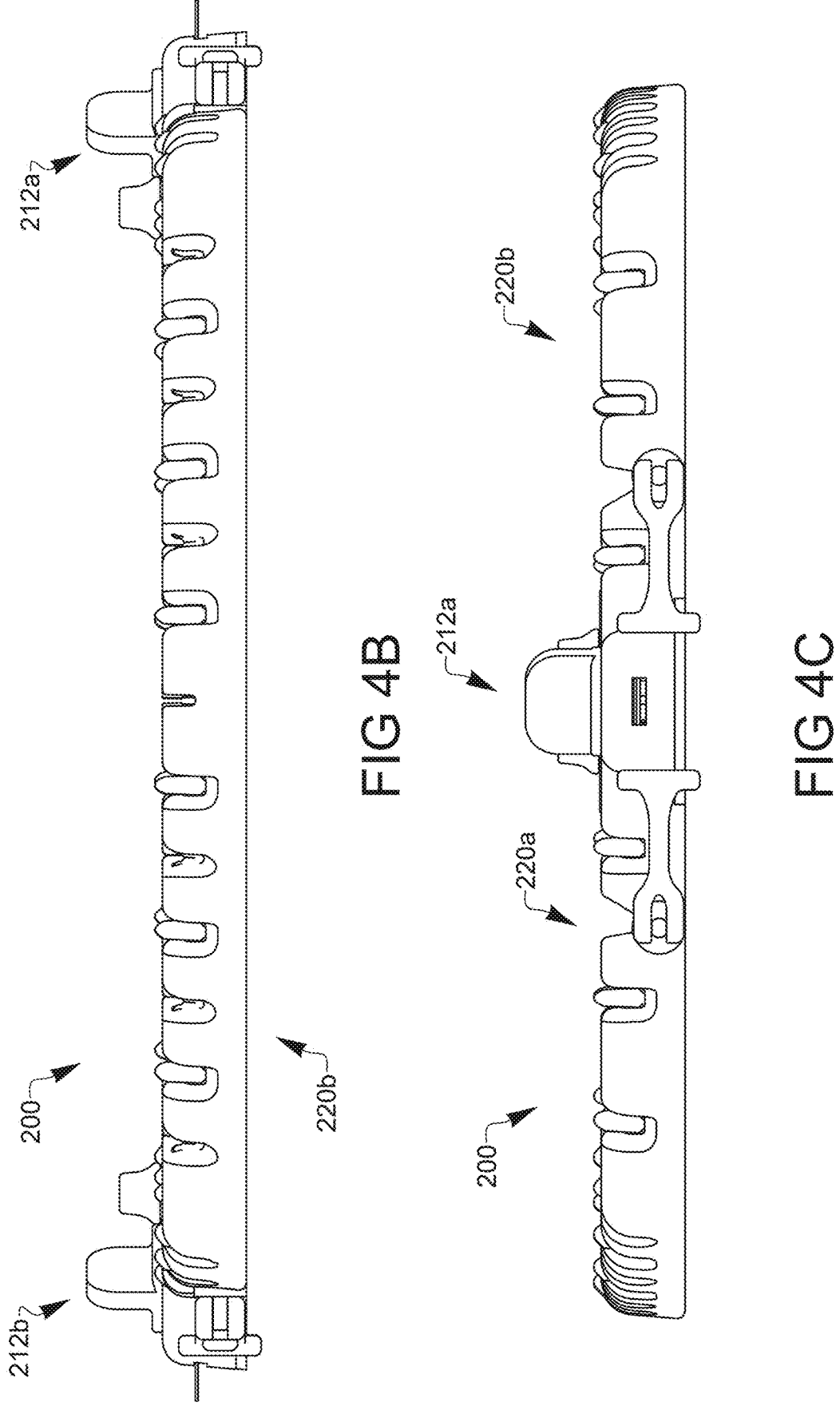
Figure 4D:
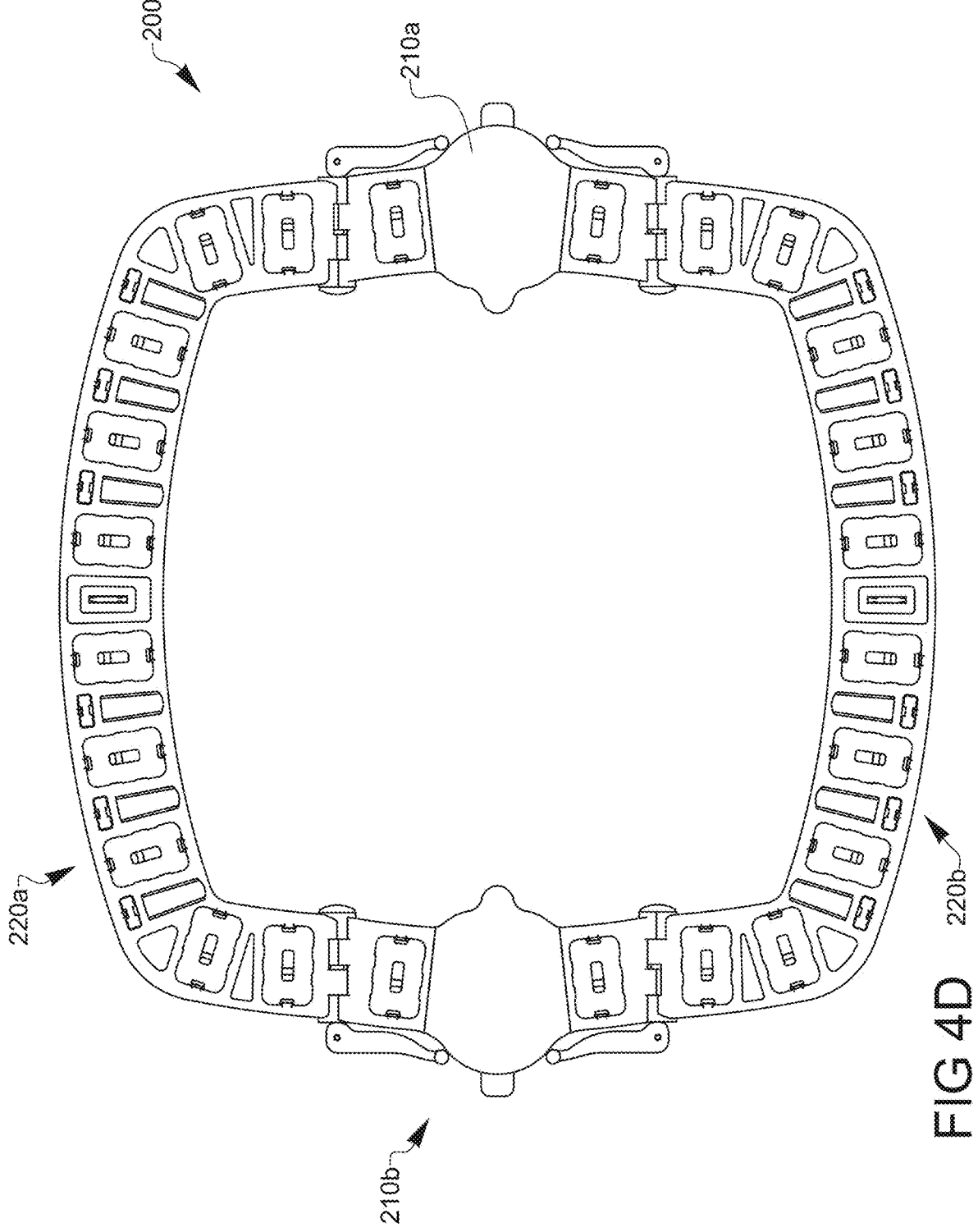
Figure 4E:
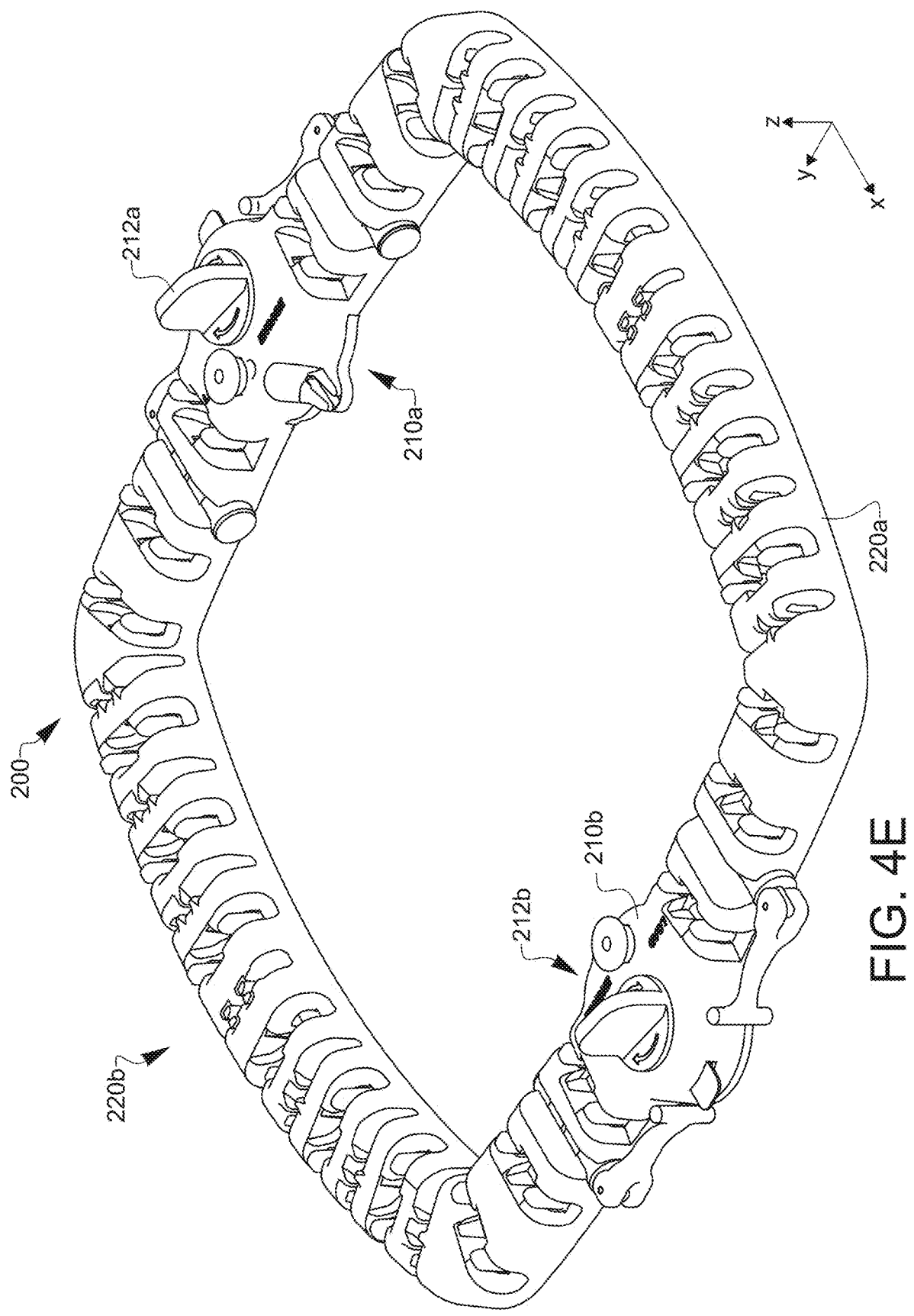

As illustrated in FIGS. 1D, 1E, and 3A, the retractor body assembly 12 may also include a first secondary retractor blade assembly 40a comprising a base portion 42a including a first base portion 44a coupled to a second base portion 46a, and the base portion 42a may extend along a base axis 48a (illustrated in FIG. 3C) from a first end to a second end. The first base portion 44a may be pivotably coupled to the second base portion 46a, such as by a living hinge. The first base portion 44a may include a first engagement feature 50a disposed at a portion of the first base portion 44a. The first engagement feature 50a may be any feature configured to receive, accept, couple to, or mate with, the first engagement feature 24a (and/or the second engagement feature 26a) of the primary retractor blade assembly 14a. For example, the first engagement feature 24a of the primary retractor blade assembly 14a may be the protrusion previously described, and the first engagement feature 50a of the first secondary retractor blade assembly 40a may be a recess, notch, or slot configured to receive the protrusion, and the undercut of the protrusion may engage a surface of (or adjacent to) the first engagement feature 50a to lock the protrusion in the first engagement feature 50a.

The second base portion 46a may include a second engagement feature 52a disposed at a portion of the second base portion 46a. The second engagement feature 52a may be any feature configured to receive, accept, couple to, or mate with, the first engagement feature 24b (and/or the second engagement feature 26b) of the second primary retractor blade assembly 14b, and the second engagement feature 52a may be identical to the first engagement feature 50a. For example, the first engagement feature 24b of the second primary retractor blade assembly 14b may be the protrusion previously described, and the second engagement feature 52a of the first secondary retractor blade assembly 40a may be a recess, notch, or slot configured to receive the protrusion, and the undercut of the protrusion may engage a surface of (or adjacent to) the second engagement feature 52a to lock the protrusion in the second engagement feature 52a.

With reference to FIG. 3A, the first secondary retractor blade assembly 40a also includes a blade portion 56a extending from a first end 58a to a second end 60a, the first end 58a of the blade portion 56a coupled to a portion of the base portion 42a, and a first portion of the blade portion 56a may be coupled to the first base portion 44a and a second portion of the blade portion 56b may be coupled to the second base portion 46a. The blade portion 56a may be substantially identical or similar to the blade portion 28a of the first primary retractor blade assembly 14a. That is, the blade portion 56a may be configured to be flexible such that the second end 60a of the blade portion 56a is configured to be displaceable relative to the first end 58a such that the second end 60a is capable of being folded away from the first end 58a and anchored to a surgical instrument (such as to a portion of the ring assembly 200 illustrated in FIGS. 4A to 4E), thereby creating a "sling" or pocket that is configured to receive and retract a corresponding portion of a patient's tissue 300, as illustrated in FIGS. 5 and 6. A coupling portion 68a may be disposed at the second end 60a of the blade portion 56a, and the coupling portion 68a may include an aperture that is configured to be coupled to a portion of a surgical instrument to provide external support for the blade portion 56a, such as a hook portion (not shown) that may be adjustably coupled to the ring assembly 200 illustrated in FIGS. 4A to 4E. The coupling portion 68a may alternatively include an elongated coupling strip 70a that extends from the second end 60a of the blade portion 56a, as illustrated in FIG. 3A. The coupling strip 70a may be engaged or secured by a portion of the ring assembly 200, or may be engaged by an adjustment gear (similar to the adjustment gear 208a) disposed at a portion of the ring assembly 200.

At least a first portion 62a of the blade portion 56a may be planar (and may be manufactured in a planar orientation), and the plane may be folded or curved about a single axis when assembled as described and as illustrated in FIG. 1A. A second portion 64a of the blade portion 56a may be non-planar, and the second portion 64a may have a sinusoidal shape (or an undulating or zig-zag) that is configured to expand in a direction along a longitudinal axis (i.e., along or parallel to the Y-axis of the reference coordinate system of FIGS. 1A, 1B, 1D, 3A, and 3C) of the blade portion 56a. The second portion 64a may act like a spring to allow the blade portion 56a to increase in length when necessary when secured to the ring assembly 200, thereby providing extra flexibility of the blade portion 56a when the blade portion 56a contacts tissue. The blade portion 56a may include a plurality of elongated tines 66a that each extend from the first end 58a to the second end 60a of the blade portion 56a. The base portion 42a, blade portion 56a, and coupling portion 68a may be a is a single, unitary part made form a single piece of material, such as a plastic material that may be injection molded as a single part.

The retractor body assembly 12 may also include a second secondary retractor blade assembly 40b that may be identical or substantially identical to, and/or a mirror-image of, the first secondary retractor blade assembly 40a. Accordingly, all reference numbers corresponding to the first secondary retractor blade assembly 40a will be identical for the second secondary retractor blade assembly 40b, with the exception that the "a" associated the first secondary retractor blade assembly 40a is replaced by a "b" for the second secondary retractor blade assembly 40b.

So configured, the base portion 16a of the first primary retractor blade assembly 14a, the base portion 42a of first secondary retractor blade assembly 40a, the base portion 16b of the second primary retractor blade assembly 14b, and the base portion 42b of first secondary retractor blade assembly 40b may be coupled together (e.g., snapped together) to form a ring having an oval shape that provides a stable base for the retractor body assembly 12. In some embodiments, as illustrated in FIG. 1E, the first engagement feature 50a of the base portion 42a of the first secondary retractor blade assembly 40a may receive, accept, couple to, or mate with, the first engagement feature 24a of the base portion 16a of the first primary retractor blade assembly 14a, and the second engagement feature 52*a* of the base portion 42*a* of the first secondary retractor blade assembly 40*a* may receive, accept, couple to, or mate with, the first engagement feature 24*b* of the base portion 16*b* of the second primary retractor blade assembly 14*b*. In addition, the first engagement feature 50*b* of the base portion 42*b* of the second secondary retractor blade assembly 40*b* may receive, accept, couple to, or mate with, the second engagement feature 26*a* of the base portion 16*a* of the first primary retractor blade assembly 14*a*, and the second engagement feature 52*b* of the base portion 42*b* of the second secondary retractor blade assembly 40*b* may receive, accept, couple to, or mate with, the second engagement feature 26*b* of the base portion 16*b* of the second primary retractor blade assembly 14*b*.

Figure 7:
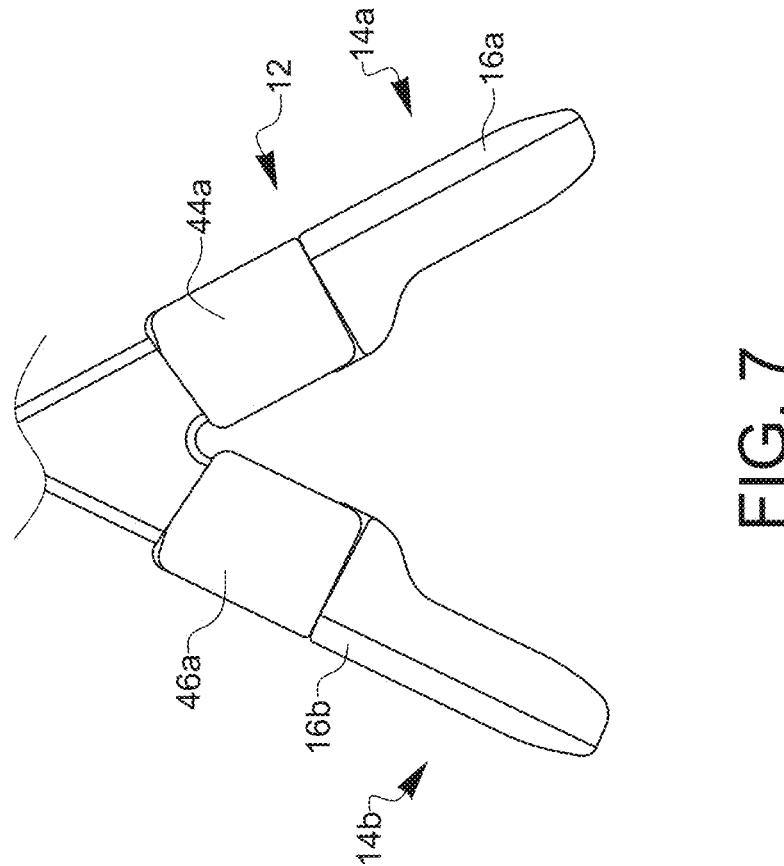
FIG. 7 is a front view of the embodiment of the retractor body assembly of FIG. 1A folded in an insertion configuration (with the first and second secondary retractor blade assemblies omitted for clarity)

During a procedure, the retractor body assembly 12, with the base portions 16*a*, 16*b*, 42*a*, 42*b* assembled as described, may be "folded" to reduce the footprint of the device for insertion into an incision 302 of a patient, as illustrated in FIGS. 5 and 6. This configuration of the retractor body assembly 12 allow it to be inserted into a relatively small incision, such as an intercostal incision of approximately 5 cm, thereby minimizing the size of the incision. As illustrated in FIG. 7, the first base portions 44*a*, 44*b* (and the first primary retractor blade assembly 14*a* coupled to the first base portions 44*a*, 44*b*) be pivoted about the living hinge relative to the second base portions 46*a*, 46*b* (and the second primary retractor blade assembly 14*b* coupled to the second base portions 46*a*, 46*b*) to "fold" the retractor body assembly 12 to allow the retractor body assembly 12 to be inserted into the incision 302 and then deployed (or "unfolded") to position the base portions 16*a*, 16*b* of the first and second primary retractor blade assemblies 14*a*, 14*b* in a desired position, then fold the second end 32*a*, 32*b* of each of the blade portion 28*a*, 28*b* to retract the tissue surrounding the incision 302, and then connect each of the coupling portions 34*a*, 34*b* to a surgical instrument, as previously described.

The folded retractor body assembly 12 may be introduced into a body cavity of a patient (e.g., by way of the incision 302) using an introducer device 400 that is illustrated in FIGS. 8A to 8H. Referring to the side view of FIG. 9B, the introducer device 400 includes a base member 402 that is elongated and extends along a base axis 404 from a proximal end 406 to a distal end 408. The base axis 404 may be parallel to the X-axis of the reference coordinate system of FIGS. 8A and 8B. The base member may 402 include a grip portion 410 and a tip portion 412. The grip portion 410 extends from the proximal end 406 to an intermediate portion 414 of the base member 402, and the tip portion 412 extends from the intermediate portion 414 of the base member 402 to the distal end 408 of the base member 402. The grip portion 410 may include two opposing lateral walls 416*a*, 416*b* that may each be planar and may each extend parallel to the X-Z plane of the reference coordinate system of FIGS. 8A and 8B. The grip portion 410 may also include a planar bottom wall 418 that may extend between bottom edges of each of the two opposing lateral walls 416*a*, 416*b*, and the bottom wall 418 may extend parallel to the X-Y plane of the reference coordinate system of FIGS. 8A and 8B. The lateral walls 416*a*, 416*b* and the bottom wall 418 may cooperate to at least partially define a base interior portion 420 (illustrated in the cross-sectional view of FIG. 9I) that may be substantially rectangular or square in shape when viewed along the base axis 404.

The tip portion 412 may also be defined by two opposing lateral walls 422*a*, 422*b* that may be planar but may have a contoured shape. In particular, as illustrated in the top view of the introducer device 400 in FIG. 8D, each of the lateral walls 422*a*, 422*b* may have a "teardrop" shape when viewed along an axis parallel to the Z-axis of the reference coordinate system of FIGS. 8A and 8B. That is, each of the lateral walls 422*a*, 422*b* may gradually diverge from the base axis 404 from a proximal end of the tip portion 412 towards a distal end of the tip portion 412 to a corresponding intermediate point 423*a*, 423*b*, at which point the each of the lateral walls 422*a*, 422*b* may gradually converge towards the base axis 404 from the corresponding intermediate point 423*a*, 423*b* to the distal end of the tip portion 412, which is the distal end 408 of the base member 402. Further, all or a portion of a top edge 424*a*, 424*b* of each of the lateral walls 422*a*, 422*b* (illustrated in the side views of FIGS. 8B and 8C) may be contoured or cambered. For example, a first portion of the top edge 424*a*, 424*b* of each of the lateral walls 422*a*, 422*b* may have a convex shape (when viewed normal or substantially normal to the plane formed by the corresponding portion of the lateral walls 422*a*, 422*b*). In some embodiments, the convex shape may be a segment of a circle, that extends from a first end at or adjacent to the distal end of the lateral walls 422*a*, 422*b* to a second end 425*a*, 425*b* distal to the proximal end of the lateral walls 422*a*, 422*b*. A second portion of the top edge 424*a*, 424*b* of each of the lateral walls 422*a*, 422*b* may have a linear or substantially linear shape (when viewed normal or substantially normal to the plane formed by the corresponding portion of the lateral walls 422*a*, 422*b*), and the second portion of the top edge 424*a*, 424*b* may extend from the second end 425*a*, 425*b* towards the proximal end of the lateral wall 422*a*, 422*b*, to a point be adjacent to the intermediate point 423*a*, 423*b*.

Figure 8A:
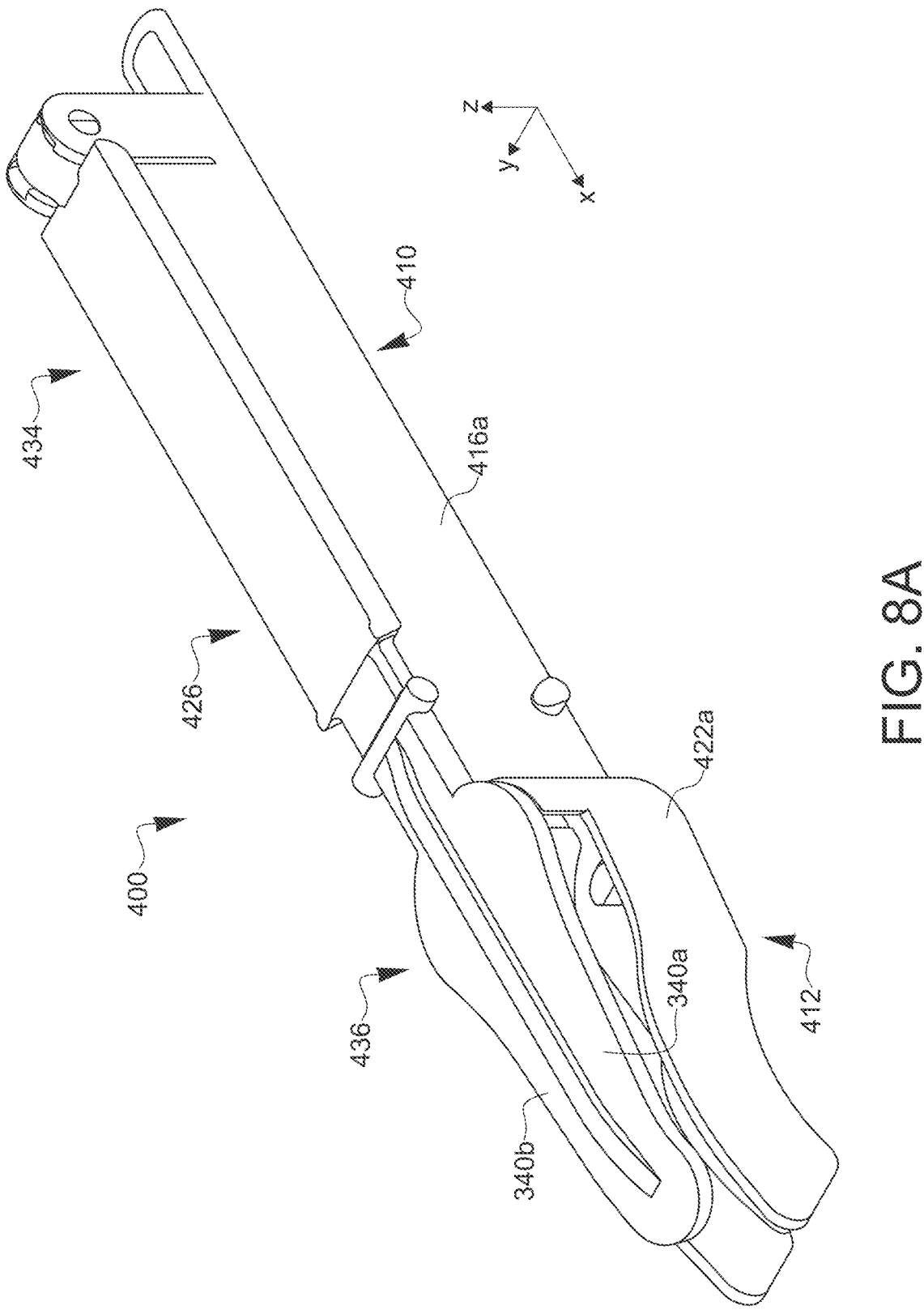
FIGS. 8A to 8H are various view of an introducer device.

Referring to the perspective view of FIG. 8A, the introducer device 400 may also include a top member 426 that may be coupled to a portion of the base member 402 such that the top member 426 may displace from a first open position (illustrated in FIG. 8H), in which the retractor body assembly 12 may be positioned within, attached to, or released from the introducer device 400, to a second closed position, which is pictured in FIGS. 9A to 10D, in in which the retractor body assembly 12 is secured to the introducer device 400 such that the retractor body assembly 12 may be introduced within a patient's body cavity.

Figures 8B, 8C:
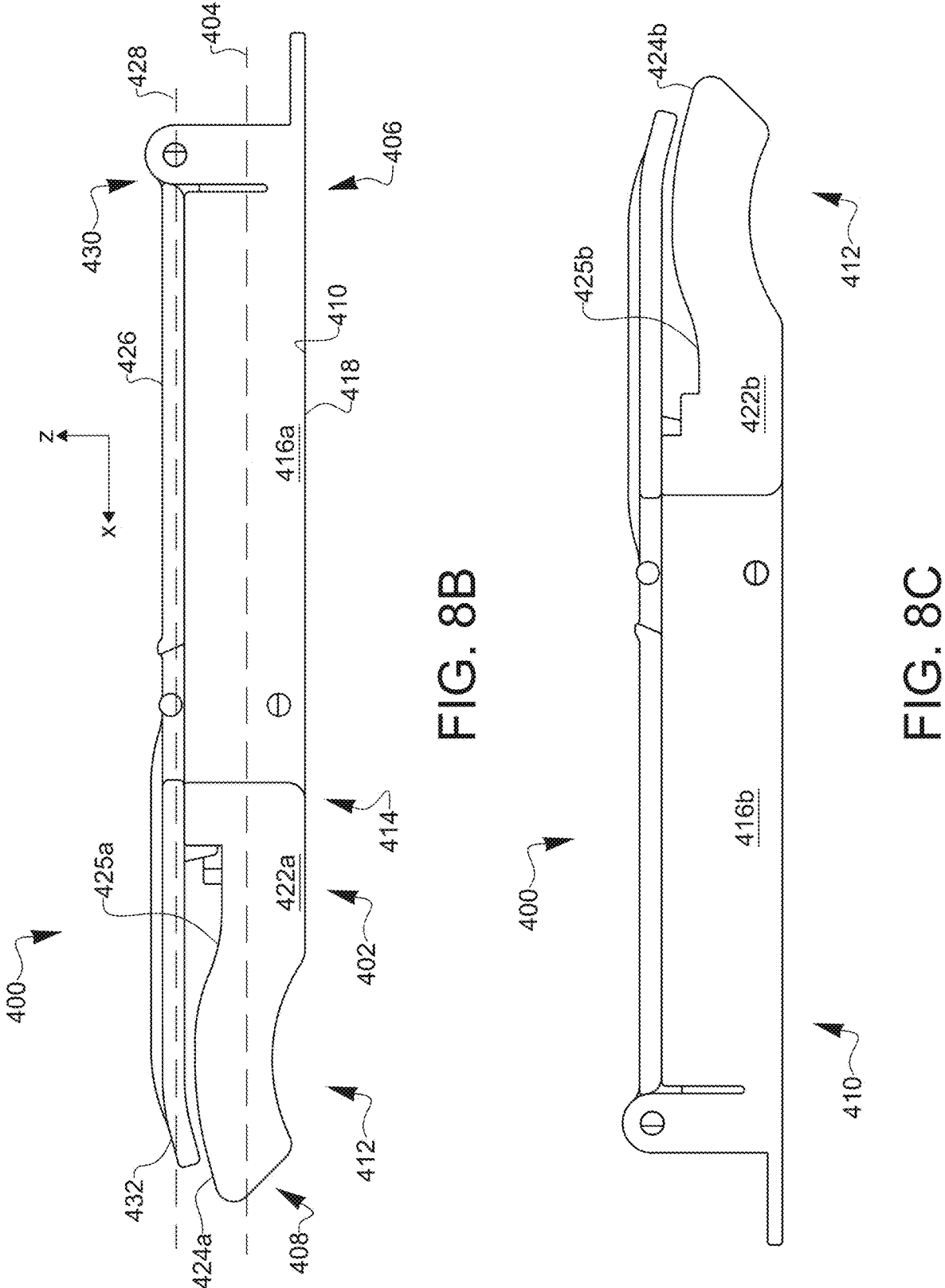
Figures 8D, 8E:
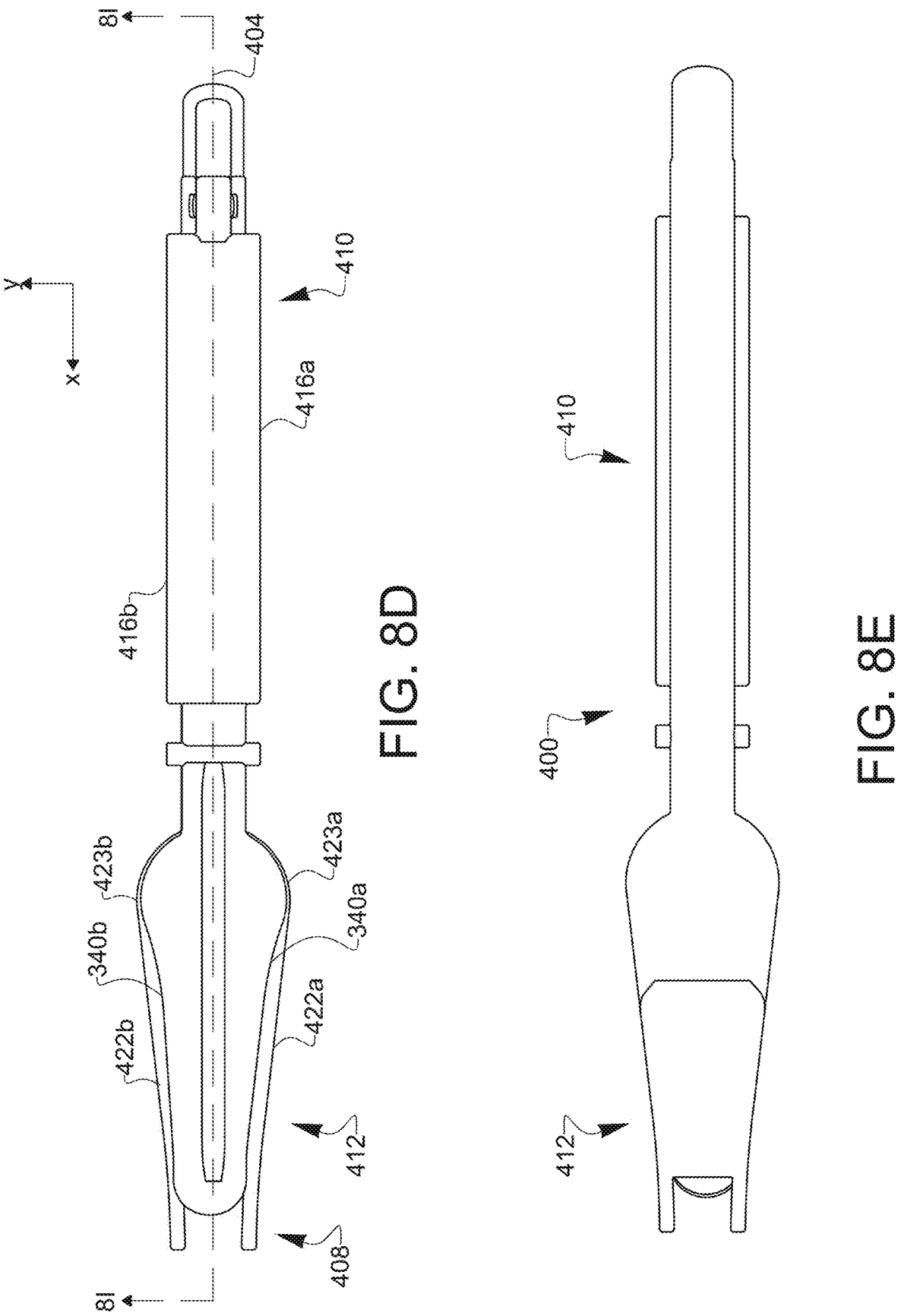
Figures 8F, 8G, 8H:
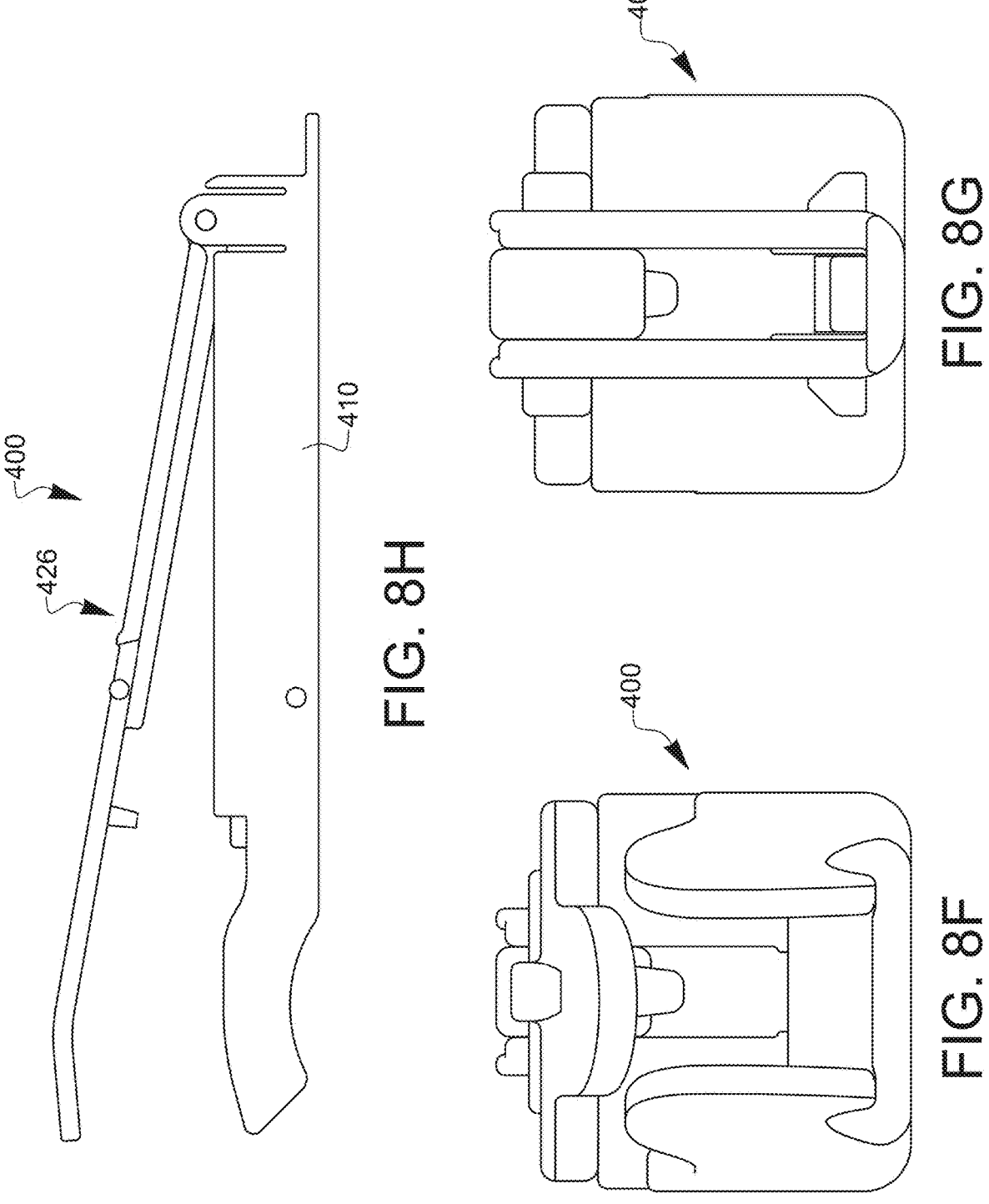

With reference to FIG. 8B, the top member 426 may be elongated and may extend along a top axis 428 from a proximal end 430 to a distal end 432. The top axis 428 may be parallel to the base axis 404 when the introducer device 400 is in the second closed position. Also in the second closed position, the proximal end 430 of the top member 426 may be at or adjacent to the proximal end 406 of the base member 402 and the distal end 432 of the top member 426 may be at or adjacent to the distal end 408 of the base member 402. The top member 426 may be planar or substantially planar and may extend parallel to the X-Y plane of the reference coordinate system of FIGS. 8A and 8B when the introducer device 400 is in the second closed position. Referring to FIG. 8A, the top member 426 may have a proximal portion 434 and a tip portion 436. The proximal portion 434 may have a width defined by opposing lateral edges that corresponds or generally corresponds to the width of the two opposing lateral walls 416*a*, 416*b* of the grip portion 410 of the base member 402. The proximal portion 434 may have a length (i.e., a dimension along an axis parallel to the X-axis of the reference coordinate system of FIGS. 8A and 8B) that corresponds or generally corresponds to the length of the two opposing lateral walls 416*a*, 416*b* of the grip portion 410 of the base member 402. When in the closed position, a bottom surface of the proximal portion 434 may further define the base interior portion 420. Further, the tip portion 436 of the top member 426 may have a profile that corresponds or generally corresponds to the profile of the tip portion 412 of the base member when viewed along an axis parallel to the Z-axis of the reference coordinate system of FIGS. 8A and 8B and when the introducer device 400 is in the second closed position. That is, the tip portion 436 may be defined by opposing lateral edges 340a, 340b that have a shape that is identical or similar to the "teardrop" shape of the lateral walls 422a, 422b of the tip portion 412 when viewed along an axis parallel to the Z-axis of the reference coordinate system of FIGS. 8A and 8B.

The top member 426 may be coupled to the base member 402 in any suitable manner. For example, the top member 426 may be pivotably coupled to the base member 402 about a hinge/pin that may be disposed at the proximal end 430 of the top member 426 and/or the proximal end 406 of the base member 402. Thus, the top member 426 may be pivotably relative to the base member 402 from the first open position to the second closed position, and vice versa.

Figure 9A:
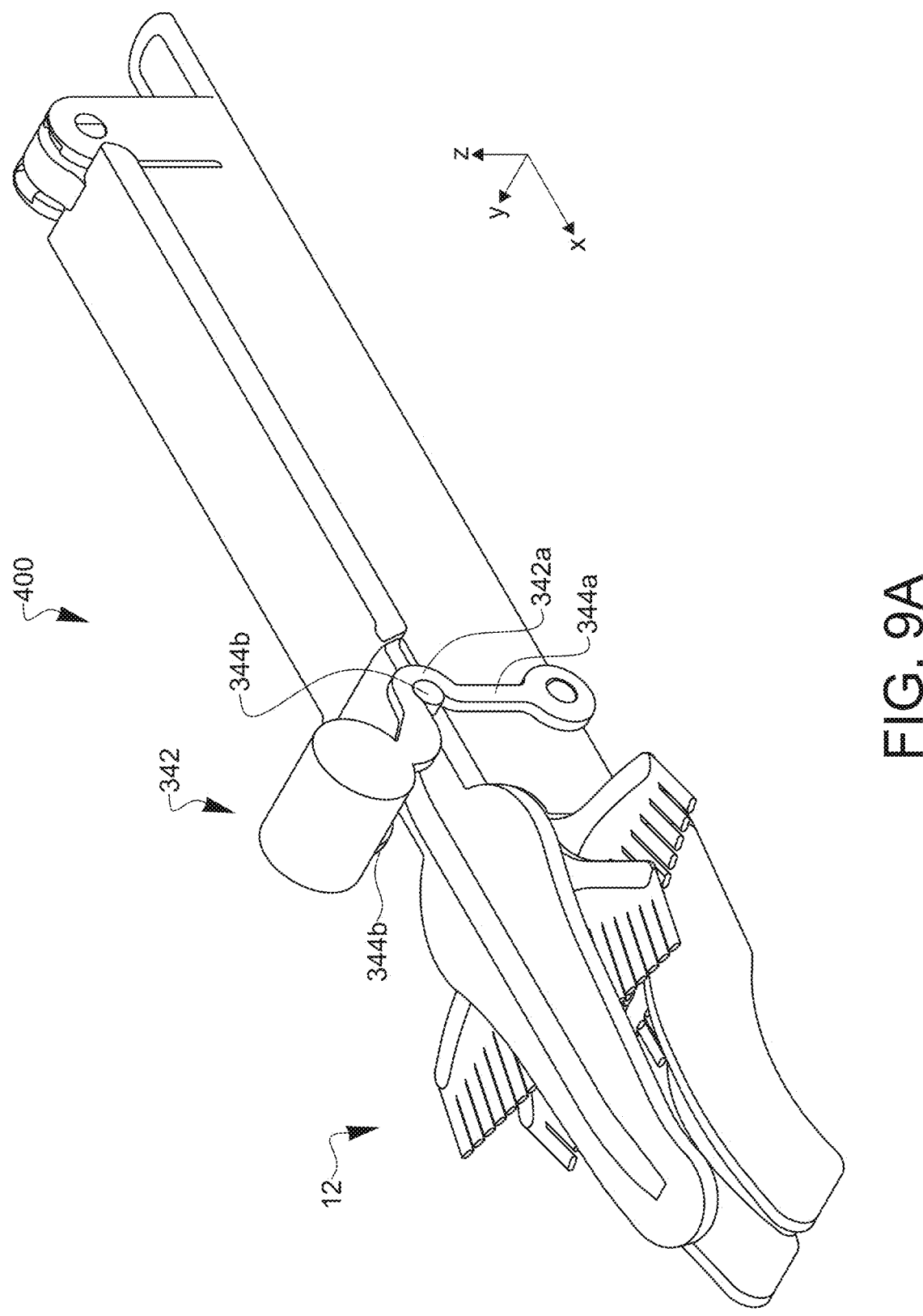
FIGS. 9A to 9I are various view of the introducer device securing the retractor body assembly (with portions of the retractor body assembly omitted for clarity)
Figures 9B, 9C:
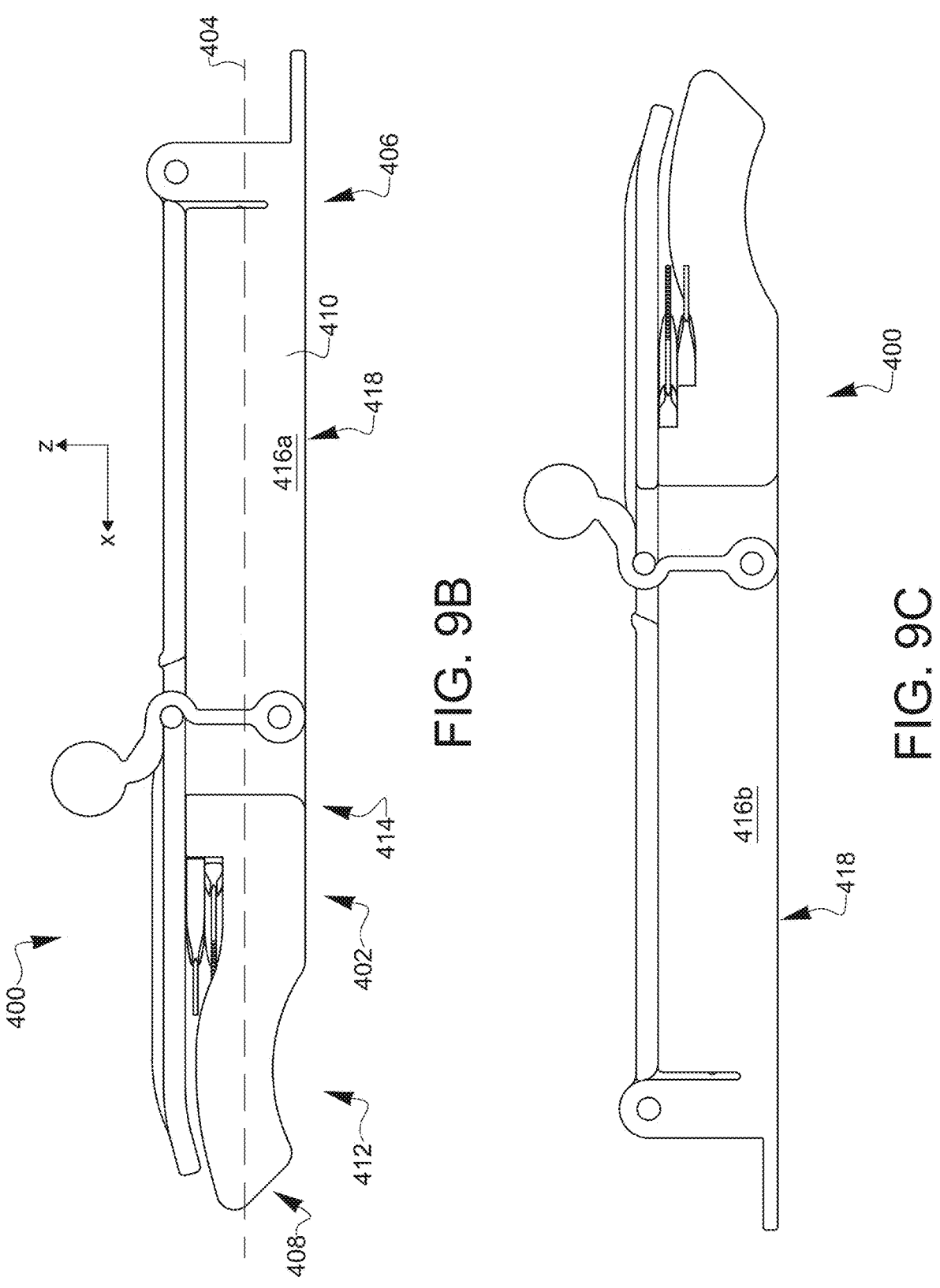
Figures 9D, 9E:
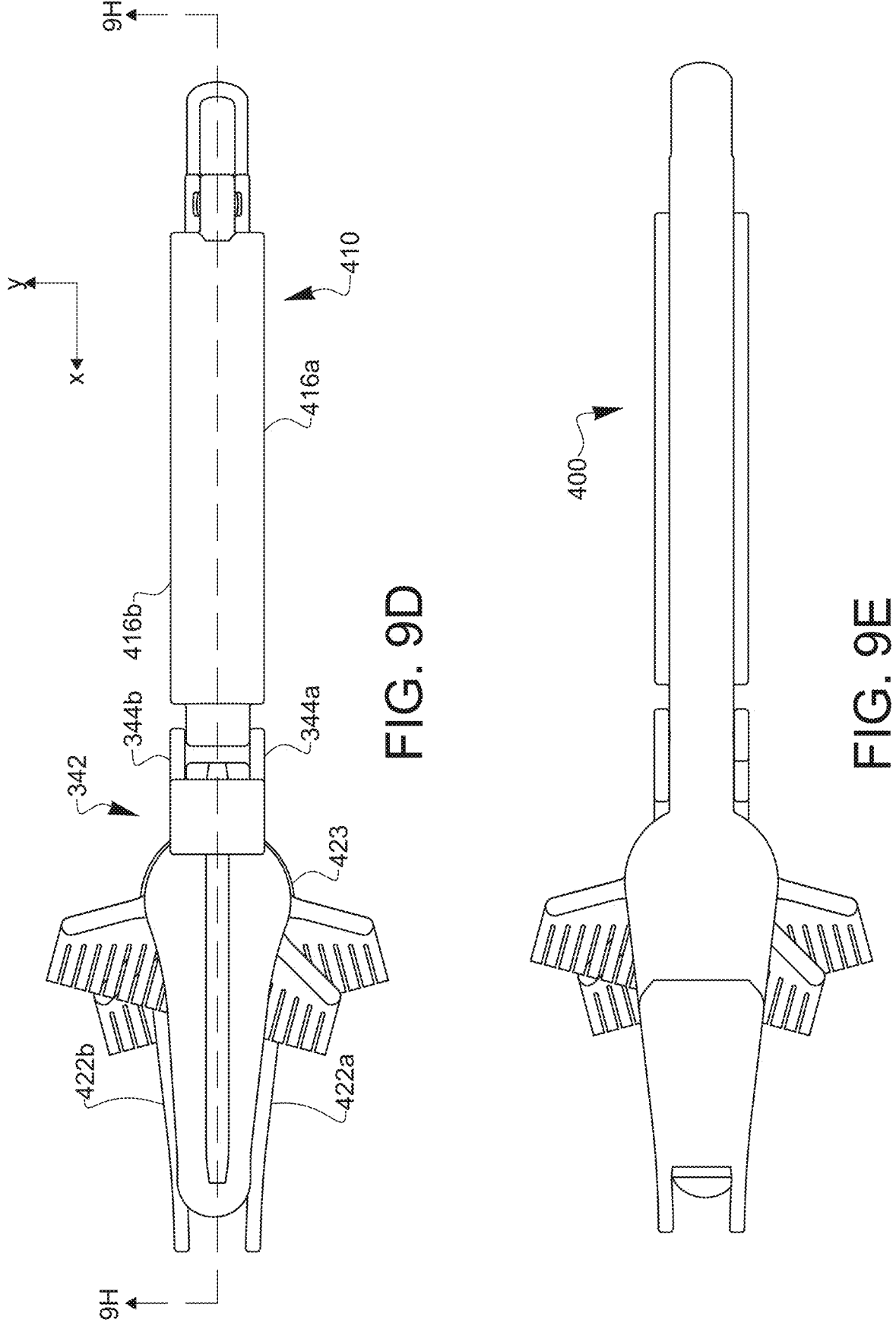
Figures 9F, 9G:
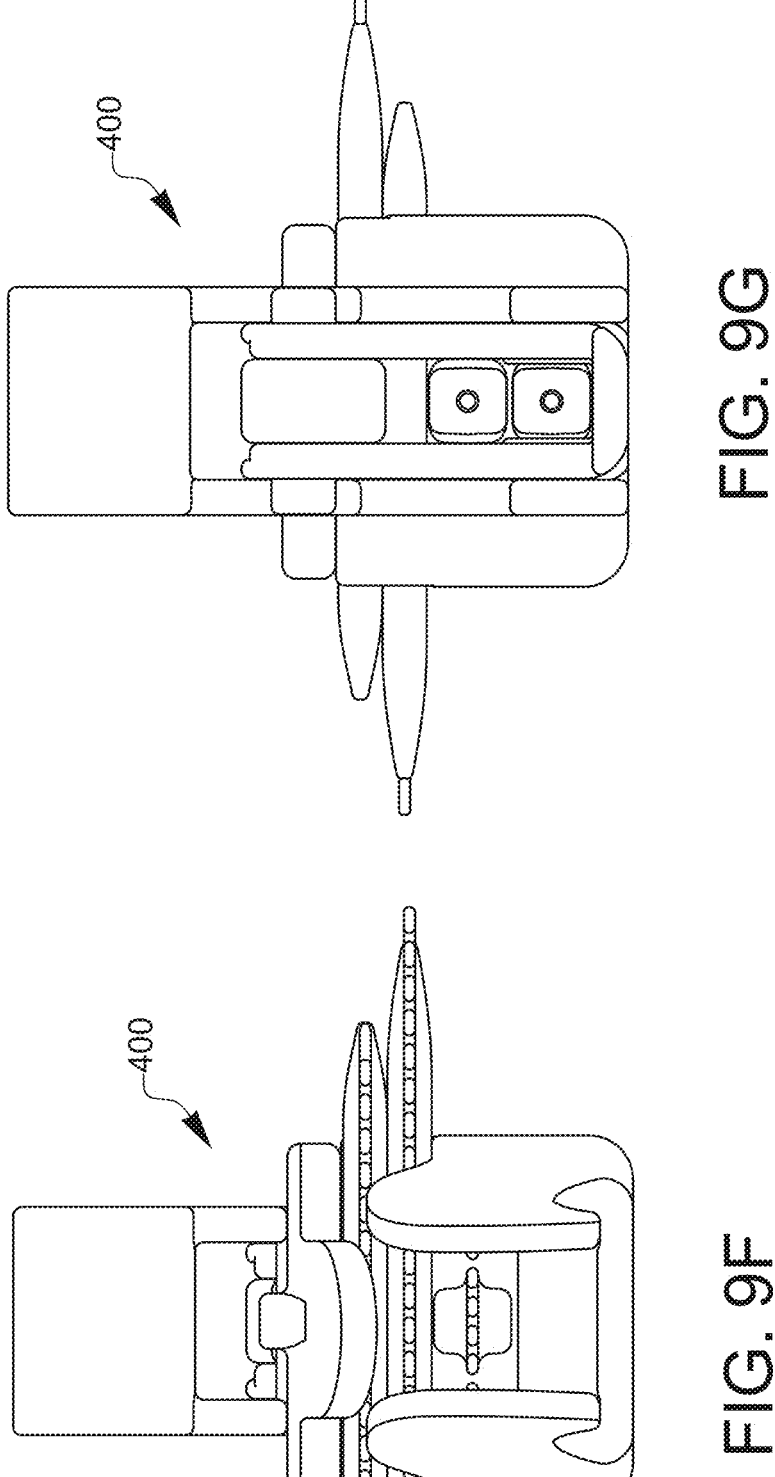
Figures 9H, 9I:
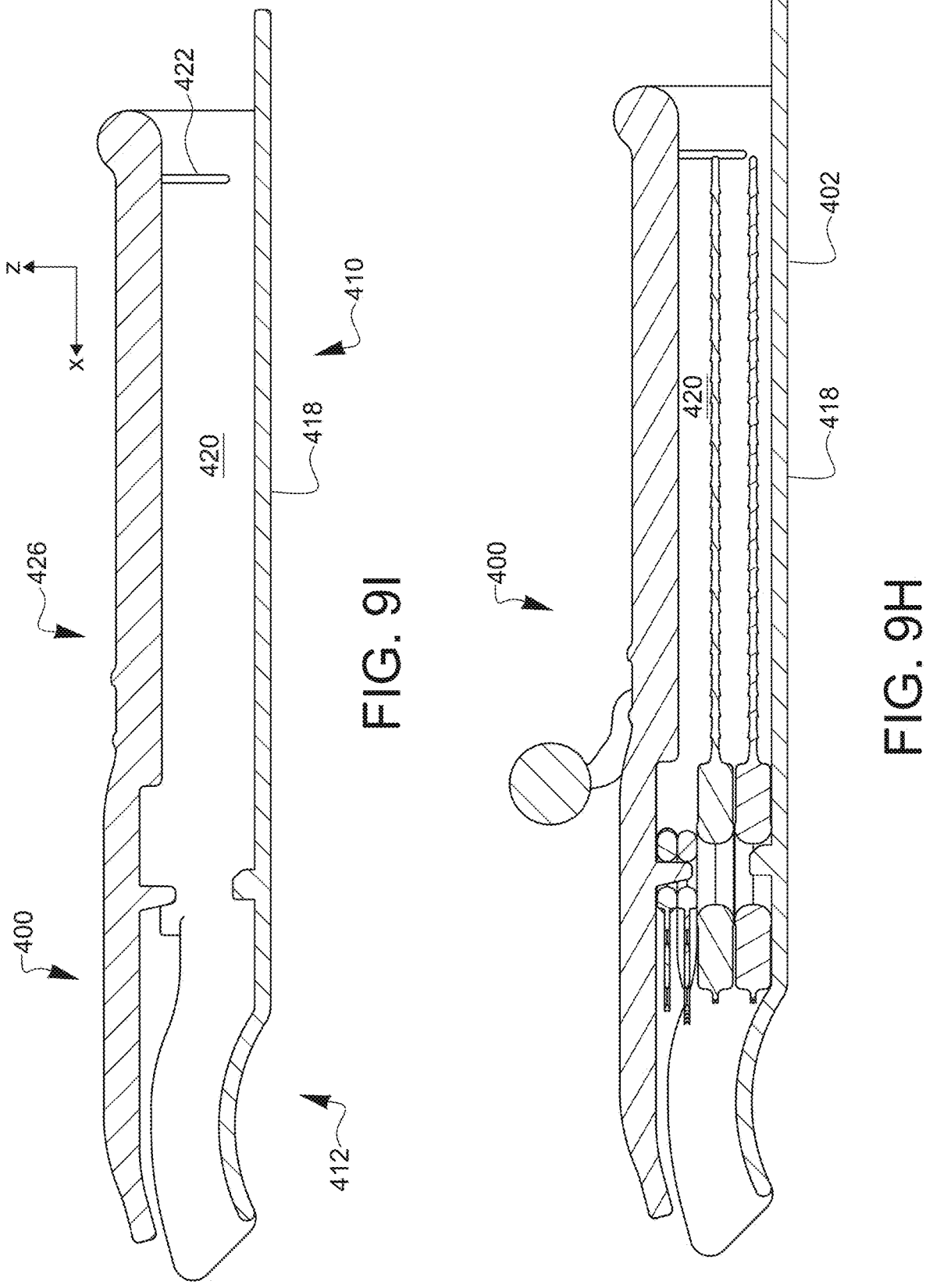
Figure 10A:
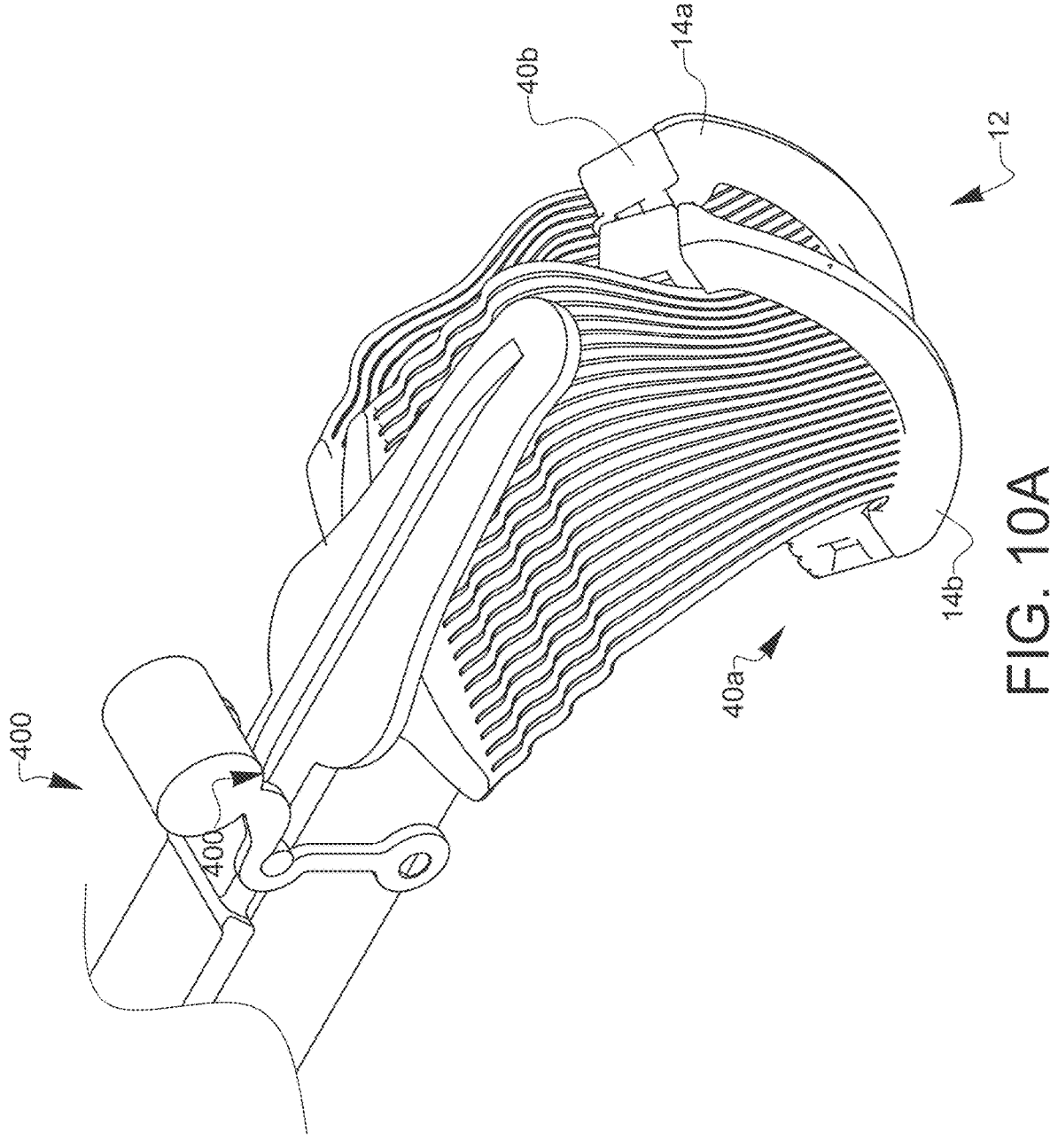
FIGS. 10A to 10D are various view of the introducer device securing the retractor body assembly.
Figure 10B:
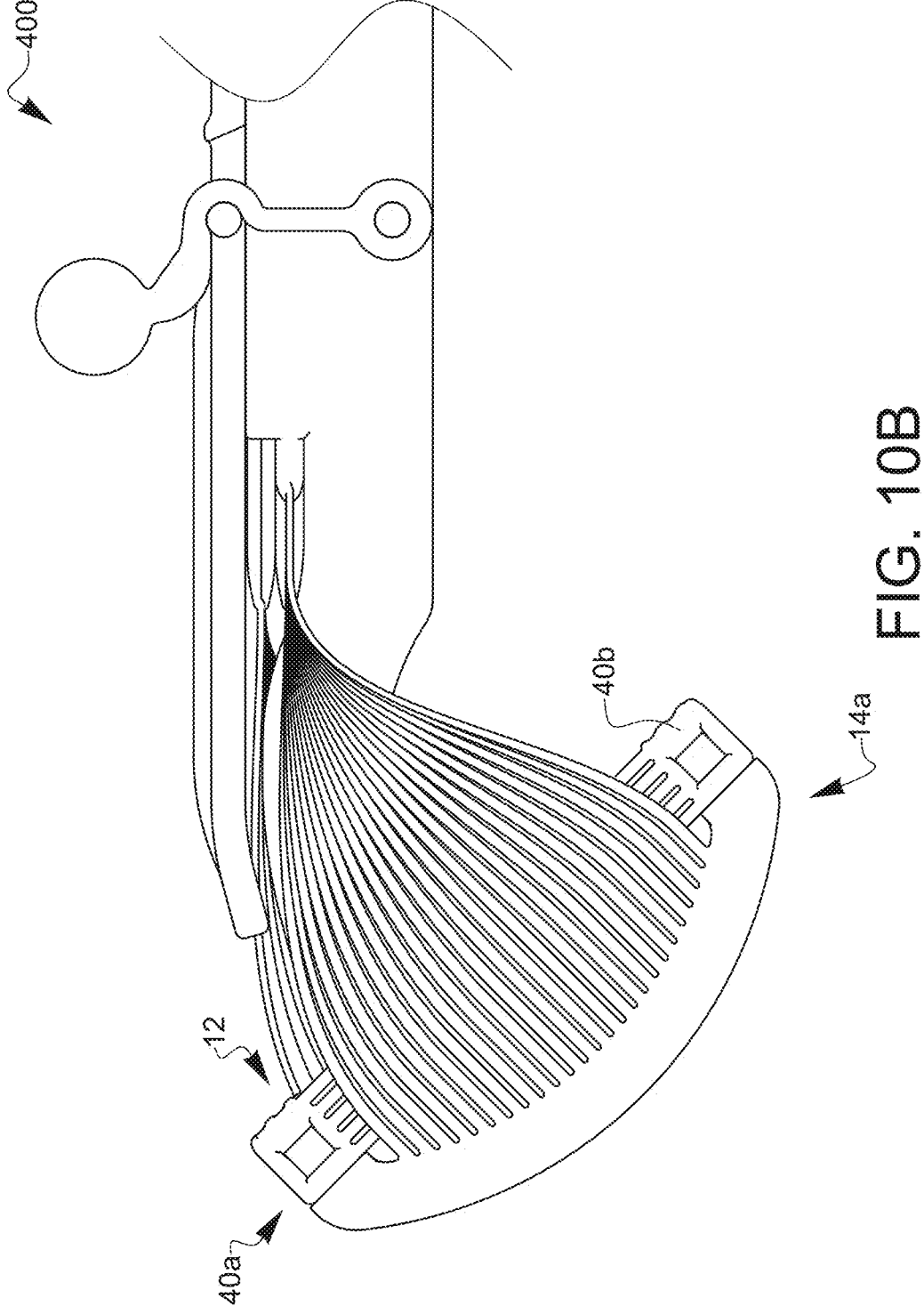
Figure 10C:
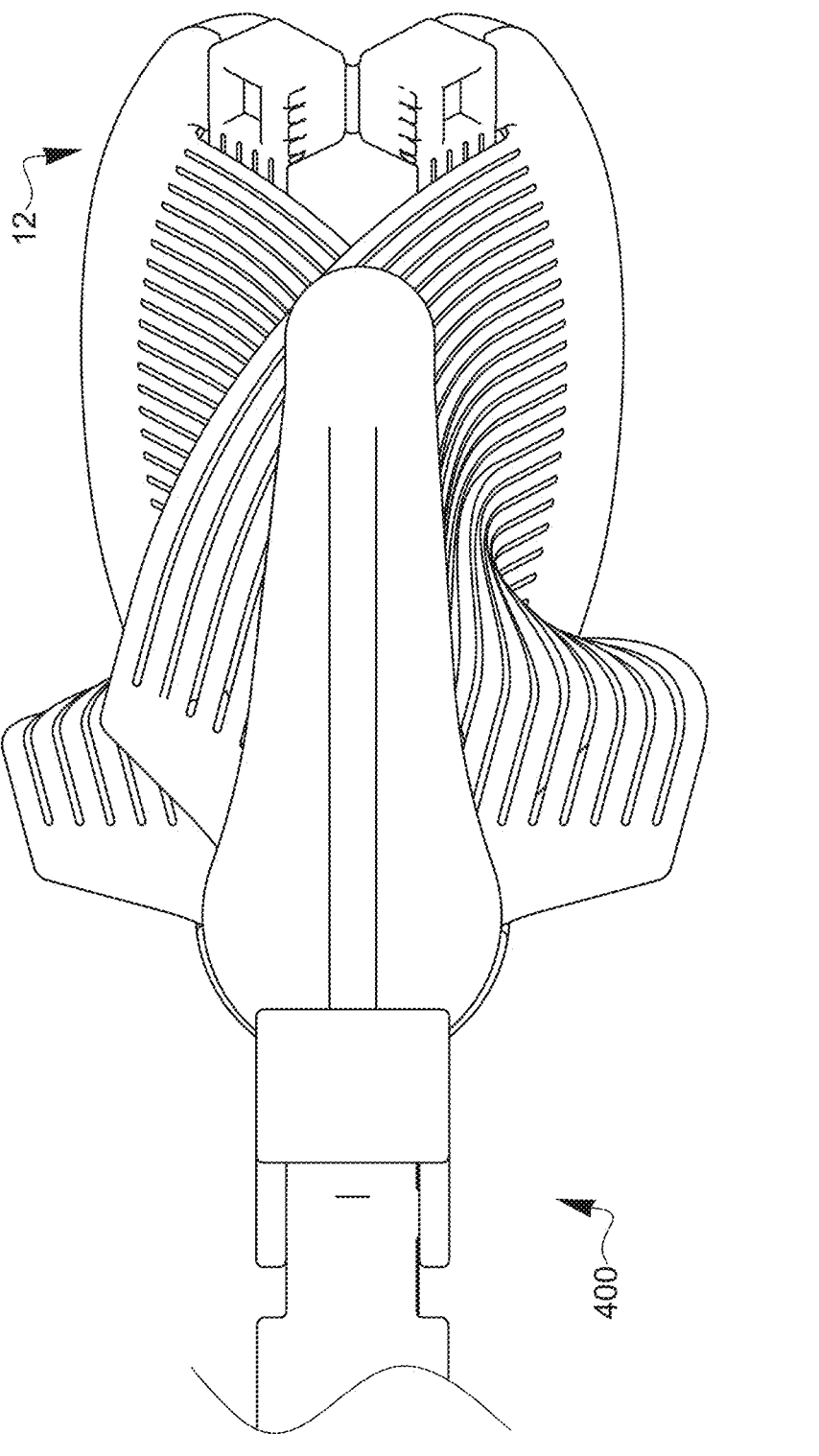
Figure 10D:
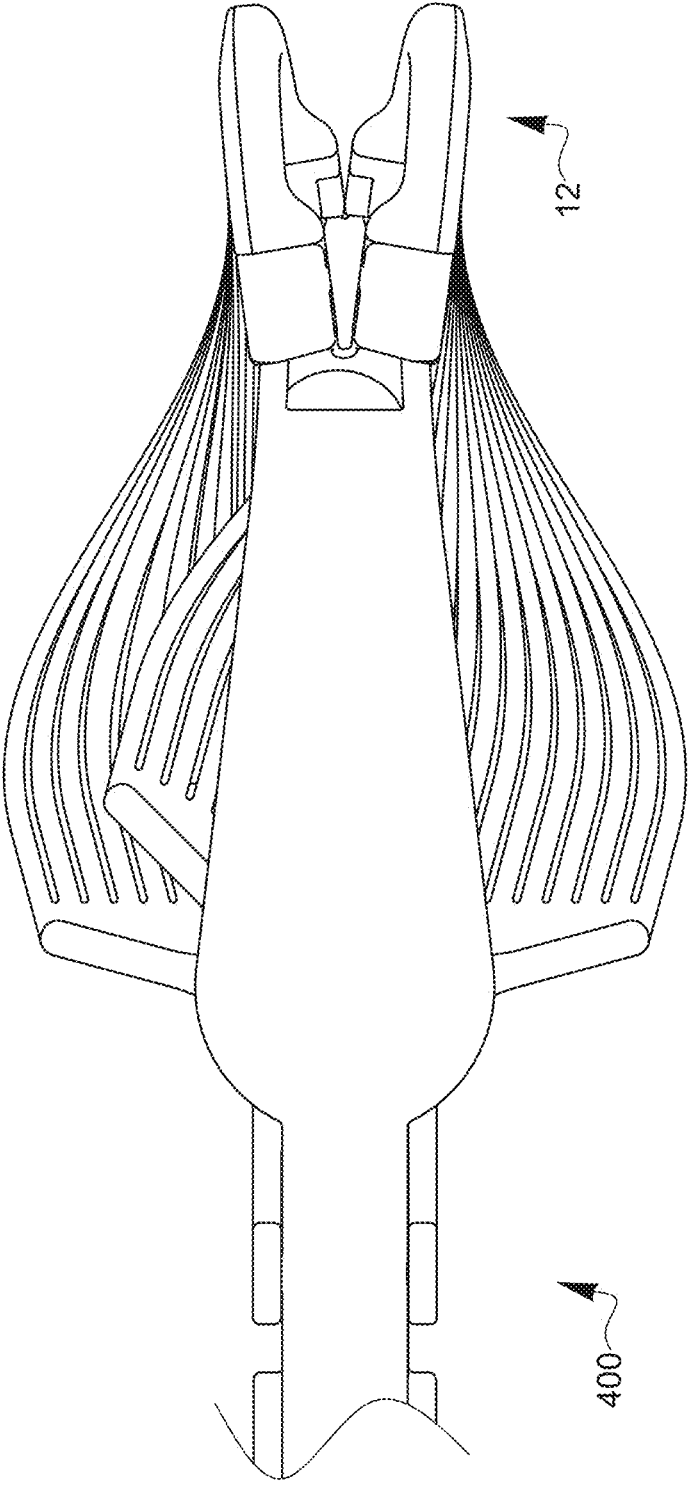

The top member 426 may be releasably locked or releasably secured to the base member 402 when in the second closed position in any suitable manner. For example, as illustrated in FIG. 9A, introducer device 400 may include a locking member 342 may have a pair of opposing arms 344a, 344b and a cross member 346 may extend between a first end portion of each of the opposing arms 344a, 344b, and the cross member 346 is configured to be gripped by a user when pivoting the locking member 342. A second end portion of each of the opposing arms 344a, 344b may be pivotably coupled to a corresponding portion of the base member, such that the locking member 342 pivots about an axis extending through the second end portion of each of the opposing arms 344a, 344b. When the locking member 342 is pivoted into a locking position (illustrated in FIG. 9A), a notch 342a, 342b on each of the opposing arms 344a, 344b receives a corresponding post or portion of a post 344a, 344b of the top member 426 to secure the top member 426 to the base member 402 in the second closed position. When it is desired to pivot the top member 426 to the first open position relative to the base member 402, the cross member 346 may be pushed proximally to disengage the post 344a, 344b of the top member 426 from the corresponding notch 342a, 342b on each of the opposing arms 344a, 344b, thereby pivoting the locking member 342 into a locked position in which the top member 426 may pivot relative to the base member 402.

When the introducer device 400 is in the first open position, the retractor body assembly 12 may be positioned within the introducer device 400. FIGS. 10A to 10D illustrate the retractor body assembly 12 secured to the introducer device 400 such that the retractor body assembly 12 may be introduced within a patient's body cavity, which FIGS. 9A to 9H illustrate the retractor body assembly 12 secured to the introducer device 400 with portions of the retractor body assembly 12 omitted for clarity. To load or couple the retractor body assembly 12 to the introducer device 400 when the introducer device 400 is in the first open position, the blade portion 28a of the first primary retractor blade assembly 14a may be folded such that a proximal portion of the blade 28a is supported by the top edge of the lateral walls 422a, 422b of the tip portion 412, and a projection 346 (see FIG. 9H) extending from a lower surface of the top member 426 may positioned within an aperture (illustrated in FIG. 2A) of the coupling portion 34a of the first primary retractor blade assembly 14a. Further, the blade portion 28b of the second primary retractor blade assembly 14b may be folded such that a proximal portion of the blade portion 28b may supported by the top edge of the lateral walls 422a, 422b of the tip portion 412 and/or the blade portion 28a of the first primary retractor blade assembly 14a, and the projection 346 (see FIG. 9H) extending from the lower surface of the top member 426 may positioned within an aperture (illustrated in FIG. 2A) of the coupling portion 34b of the second primary retractor blade assembly 14b. Thus, when the introducer device 400 is in the second closed position, the projection 346 of top member 426 extends through the apertures of the coupling portions 34a, 34b of the first and second primary retractor blade assemblies 14a, 14b, and the proximal portions of the blade portions 28a, 28b of the first and second primary retractor blade assemblies 14a, 14b are clamped between portions of the lower surface of the top member 426 and all or a portion of each of the top edges of the lateral walls 422a, 422b of the tip portion 412.

Further, the first secondary retractor blade assembly 40a may be secured such the blade portion 56a of the first secondary retractor blade assembly 40a may be folded such that a proximal portion of the blade 28a is supported by the top edge of the lateral walls 422a, 422b of the tip portion 412 and/or the blade portions 28a, 28b of the first and second primary retractor blade assembles 14a, 14b. The first secondary retractor blade assembly 40a may be further secured such that the aperture of the coupling portion 68a may be aligned with the apertures of the coupling portions 34a, 34b of the first and second primary retractor blade assemblies 14a, 14b, and the projection 346 (or a similar projection extending from the bottom wall 418 of the base member 402) may extend through the aperture of the coupling portion 68a. In this position, a projection extending from the coupling portion 68a of the first secondary retractor blade assembly 40a may extend proximally, and may be disposed within the portion of the base interior portion 420. The second secondary retractor blade assembly 40b may be secured in a similar manner, and as such, the blade portion 56b of the second secondary retractor blade assembly 40b may be folded such that a proximal portion of the blade 28a is supported by the top edge of the lateral walls 422a, 422b of the tip portion 412 and/or the blade portions 28a, 28b of the first and second primary retractor blade assembles 14a, 14b and/or the blade portion 56a of the first secondary retractor blade assembly 40a. Thus, when the introducer device is in the second closed position, proximal portions of the blade portions 28a, 28b of the first and second primary retractor blade assembles 14a, 14b and proximal portions of the blade portions 56a, 56b of the first and second secondary retractor blade assemblies 40a, 40b may be stacked and sandwiched between the top member 426 and the base member 426 to strongly secure the retractor body assembly 12 to the introducer device 400 while maintaining a "low profile" position to facilitate insertion into an incision.

In addition, the aperture of the coupling portion 68b may be aligned with the apertures of the coupling portions 34a, 34b of the first and second primary retractor blade assemblies 14a, 14b, and the projection 346 (or the similar projection extending from the bottom wall 418 of the base member 402) may extend through the aperture of the coupling portion 68b. In this position, a projection extending from the coupling portion 68b of the second secondary retractor blade assembly 40b may extend proximally, and may be disposed within a the portion of the base interior portion 420. So configured, the retractor body assembly 12 in a folded configuration may be secured to the introducer device 400 with the introducer device in the second closed position for introduction within a patient's body cavity during a procedure.

To release the retractor body assembly 12 in a desired location, the locking member 426 may be pivoted into the unlocked position or otherwise disengaged, and the top member 426 may be pivoted into the first open position relative to the base member 402, thereby releasing the clamping pressure on the blade portions 28a, 28b of the first and second primary retractor blade assembles 14a, 14b and the blade portions 56a, 56b of the first and second secondary retractor blade assemblies 40a, 40b and allowing the retractor body assembly 12 to be removed from the introducer device 400 and deployed for retraction.

As illustrated in FIG. 6, the retractor assembly 10 may include the ring assembly 200, and the retractor body assembly 12 may be coupled to the ring assembly 200. As illustrated in FIGS. 4A to 4E, the ring assembly 200 may include a first base portion 210a and a second base portion 210b, and the first base portion 210a may include the adjustment gear 208a, that comprises an interface knob 212a configured to be rotated by a user. The interface knob 212a may be coupled to any suitable mechanism to engage and retract a portion of the coupling strip 36a of the first primary retractor blade assembly 14a. For example, the interface knob 212a may be coupled to a spur gear (not shown) that is coupled to a rack (not shown) such that rotating the interface knob 212a linearly displaces the rack that may be coupled to the coupling strip 36a of the first primary retractor blade assembly 14a. In other embodiments, the rack may be coupled to a hook portion (not shown) that engages the coupling portion 34a of the first primary retractor blade assembly 14a as described.

The second base portion 210b may be identical or substantially identical to, and/or a mirror-image of, the first base portion 210a. Accordingly, all reference numbers corresponding to the first base portion 210a will be identical for the second base portion 210b, with the exception that the "a" associated the first base portion 210a is replaced by a "b" for the second base portion 210b.

The ring assembly 200 may also include a first ring arm 220a extend along a first ring arm axis from a first end to a second end, and the first ring arm 220a may be configured to support various surgical instruments or other surgical equipment or supplies (i.e., one or more portions of suture). The ring assembly 200 may also include a second ring arm 220b extend along a second ring arm axis from a first end to a second end, and the second ring arm 220b may be identical or substantially identical to, and/or a mirror-image of, the first ring arm 220a. Portions of the first ring arm 220a and the second ring arm 220b, such as one or more slots, may be configured to support or engage the coupling strip 70a, 70b of the first and second secondary retractor blade assemblies 40a, 40b. The first end of the first ring arm 220a may be pivotably coupled to a first end of the first base portion 210a and the second end of the first ring arm 220a may be pivotably coupled to a first end of the second base portion 210b such that the first ring arm 220a may pivot relative to the first and second base portions 210a, 210b. Similarly, the first end of the second ring arm 220b may be pivotably coupled to a second end of the first base portion 210a and the second end of the second ring arm 220b may be pivotably coupled to a second end of the second base portion 210b such that the second ring arm 220b may pivot relative to the first and second base portions 210a, 210b. One or more portions of any or all of the first and second base portions 210a, 210b and the first and second ring arms 220a, 220b may be anchored for fixedly attached to an external support to stabilize the ring assembly 200.

With the base portions 16a, 16b, 42a, 42b of the retractor body assembly 12 assembled as described and inserted into the incision 302 of the patient, the retractor body assembly 12 may be unfolded within the incision 302. The coupling strip 36a of the first primary retractor blade assembly 14a may be coupled to the adjustment gear 208a disposed at a portion of the ring assembly 200, and the coupling strip 36b of the second primary retractor blade assembly 14b may be coupled to the adjustment gear 208b disposed at a portion of the ring assembly 200. Further, the coupling strip 70a of the first secondary retractor blade assembly 40a may be coupled to a portion of the ring assembly 200, and the coupling strip 70b of the second secondary retractor blade assembly 40b may be coupled to a portion of the ring assembly 200. The adjustment gears 208a, 208b may be engaged to retract the blade portions 28a, 28b of the first primary retractor blade assemblies 14a, 14b to increase or decrease the size of the incision 302. Also, the positions of the coupling strips 70a, 70b of the first and second secondary retractor blade assemblies 40a, 40b may be coupled to a portion of the ring assembly 200 to retract the blade portions 56a, 56b to further adjust the size of the incision 302. The flexibility of the blade portions 28a, 28b, 56a, 56b, allows for the atraumatic contouring of the tissue defining the incision 302 while securing the retracted tissue to allow for unobstructed access through the incision 302.

Various advantages of a retractor assembly have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A retractor body assembly comprising:
   a first primary retractor blade assembly comprising:
       a base portion, the base portion extending along a base axis from a first end to a second end, the base portion including a first engagement feature disposed at a first portion of the base portion and a second engagement feature disposed at a second portion of the base portion;
       a blade portion extending from a first end to a second end, the first end of the blade portion coupled to a portion of the base portion, the blade portion configured to be flexible; and
       a coupling portion disposed at the second end of the blade portion, the coupling portion configured to be coupled to a surgical instrument to provide external support for the blade portion;
   a second primary retractor blade assembly comprising:
       a base portion, the base portion extending along a base axis from a first end to a second end, the base portion including a first engagement feature coupled to a first portion of the base portion and a second engagement feature coupled to a second portion of the base portion;

a blade portion extending from a first end to a second end, the first end of the blade portion coupled to a portion of the base portion, the blade portion configured to be flexible; and a coupling portion disposed at the second end of the blade portion, the coupling portion configured to be coupled to a surgical instrument to provide external support for the blade portion;

a first secondary retractor blade assembly comprising:

a base portion including a first base portion coupled to a second base portion, the base portion extending along a base axis from a first end to a second end, the base portion including a first engagement feature disposed at a portion of the first base portion and a second engagement feature disposed at a portion of the second base portion;

a blade portion extending from a first end to a second end, the first end of the blade portion coupled to a portion of the base portion, the blade portion configured to be flexible; and a coupling portion disposed at the second end of the blade portion, the coupling portion configured to be coupled to a surgical instrument to provide external support for the blade portion; and a second secondary retractor blade assembly comprising:

a base portion including a first base portion coupled to a second base portion, the base portion extending along a base axis from a first end to a second end, the base portion including a first engagement feature disposed at a portion of the first base portion and a second engagement feature disposed at a portion of the second base portion;

a blade portion extending from a first end to a second end, the first end of the blade portion coupled to a portion of the base portion, the blade portion configured to be flexible; and a coupling portion disposed at the second end of the blade portion, the coupling portion configured to be coupled to a surgical instrument to provide external support for the blade portion, wherein the blade portion of each of the first primary retractor blade assembly, the second primary retractor blade assembly, the first secondary retractor blade assembly, and the second secondary retractor blade assembly cooperate to maintain an incision into a tissue of a patient in a desired position during a medical procedure, wherein at least a first portion of the blade portion of the first primary retractor blade assembly is planar, and at least a first portion of the blade portion of the second primary retractor blade assembly is planar, and wherein the blade portion of the first primary retractor blade assembly includes a plurality of elongated tines that each extend from the first end to the second end of the blade portion of the first primary retractor blade assembly, and the blade portion of the second primary retractor blade assembly includes a plurality of elongated tines that each extend from the first end to the second end of the blade portion of the second primary retractor blade assembly.

2. The retractor body assembly of claim 1, wherein base axis of the base portion of the first primary retractor blade assembly is non-linear and the base axis of the base portion of the second primary retractor blade assembly is non-linear.

3. The retractor body assembly of claim 1, wherein the base axis of the base portion of the first primary retractor blade assembly has a first arcuate shape and the base axis of the base portion of the second primary retractor blade assembly has a second arcuate shape.

4. The retractor body assembly of claim 3, wherein the first arcuate shape is identical to but a mirror image of the second arcuate shape.

5. The retractor body assembly of claim 1, wherein the first engagement feature of the base portion of the first primary retractor blade assembly is disposed at or adjacent to the first end of the base portion, and the second engagement feature of the base portion of the first primary retractor blade assembly is disposed at or adjacent to the second end of the base portion, and wherein the first engagement feature of the base portion of the second primary retractor blade assembly is disposed at or adjacent to the first end of the base portion, and the second engagement feature of the base portion of the second primary retractor blade assembly is disposed at or adjacent to the second end of the base portion.

6. The retractor body assembly of claim 5, wherein each of the first engagement feature and the second engagement feature of the base portion of the first primary retractor blade assembly is a projection extending away from the base axis of the base portion of the first primary retractor blade assembly, and wherein each of the first engagement feature and the second engagement feature of the base portion of the second primary retractor blade assembly is a projection extending away from the base axis of the base portion of the second primary retractor blade assembly.

7. The retractor body assembly of claim 1, wherein a second portion of the blade portion of the first primary retractor blade assembly is non-planar, and a second portion of the blade portion of the second primary retractor blade assembly is non-planar.

8. The retractor body assembly of claim 7, wherein the second portion of the blade portion of the first primary retractor blade assembly has a sinusoidal shape that is configured to expand in a direction along a longitudinal axis of the second portion, and the second portion of the blade portion of the second primary retractor blade assembly has a sinusoidal shape that is configured to expand in a direction along a longitudinal axis of the second portion.

9. The retractor body assembly of claim 1, wherein the base portion, the blade portion, and the coupling portion of the first primary retractor blade assembly is a single, unitary part, and the base portion, the blade portion, and the coupling portion of the second primary retractor blade assembly is a single, unitary part.

10. The retractor body assembly of claim 1, wherein the first base portion of the base portion of the first secondary retractor blade assembly is pivotably coupled to the second base portion of the base portion of the first secondary retractor blade assembly.

11. The retractor body assembly of claim 1, wherein the first engagement feature of the first secondary retractor blade assembly is a recess disposed in the first base portion and the second engagement feature of the first secondary retractor blade assembly is a recess disposed in the second base portion, and wherein the first engagement feature of the second secondary retractor blade assembly is a recess disposed in the first base portion and the second engagement feature of the second secondary retractor blade assembly is a recess disposed in the second base portion.

* * * * *